(12) United States Patent
Shibata et al.

(10) Patent No.: US 8,228,494 B2
(45) Date of Patent: *Jul. 24, 2012

(54) APPARATUS FOR INSPECTING DEFECTS

(75) Inventors: Yukihiro Shibata, Fujisawa (JP); Shunji Maeda, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/198,170

(22) Filed: Aug. 4, 2011

(65) Prior Publication Data

US 2011/0292390 A1   Dec. 1, 2011

Related U.S. Application Data

(63) Continuation of application No. 12/771,216, filed on Apr. 30, 2010, now Pat. No. 8,004,666, which is a continuation of application No. 11/936,115, filed on Nov. 7, 2007, now Pat. No. 7,714,997.

(30) Foreign Application Priority Data

Nov. 7, 2006 (JP) .................................. 2006-301990
Dec. 13, 2006 (JP) .................................. 2006-336211

(51) Int. Cl.
   *G01N 21/00* (2006.01)
(52) U.S. Cl. ............... 356/237.2; 356/237.3; 356/237.4; 356/237.5
(58) Field of Classification Search ..... 356/237.1–237.5
   See application file for complete search history.

(56) References Cited

U.S. PATENT DOCUMENTS

| | | | |
|---|---|---|---|
| 6,084,664 A | 7/2000 | Matsumoto et al. | |
| 6,180,415 B1 | 1/2001 | Schultz et al. | |
| 6,411,377 B1 | 6/2002 | Noguchi et al. | |
| 7,265,900 B2 | 9/2007 | Korngut et al. | |
| 7,339,661 B2 | 3/2008 | Korngut et al. | |
| 7,714,997 B2* | 5/2010 | Shibata et al. | 356/237.2 |
| 8,004,666 B2* | 8/2011 | Shibata et al. | 356/237.2 |
| 2002/0154303 A1 | 10/2002 | Maeda et al. | |
| 2003/0081201 A1 | 5/2003 | Shibata et al. | |
| 2004/0017562 A1 | 1/2004 | Tsai et al. | |
| 2004/0042001 A1 | 3/2004 | Vaez-Iravani et al. | |
| 2005/0206888 A1 | 9/2005 | Yoshida et al. | |
| 2005/0219518 A1 | 10/2005 | Korngut et al. | |
| 2006/0078190 A1 | 4/2006 | Shibata et al. | |

FOREIGN PATENT DOCUMENTS

| | | |
|---|---|---|
| JP | 6-167458 | 6/1994 |
| JP | 08-327557 | 12/1996 |

(Continued)

*Primary Examiner* — Michael P Stafira

(74) *Attorney, Agent, or Firm* — Antonelli, Terry, Stout & Kraus, LLP.

(57) ABSTRACT

A defect inspection apparatus includes an illumination optical system, a detection optical system which includes a reflecting objective lens, and wavelength separation optics for conducting wavelength separation, and after the wavelength separation, branching the scattered light into at least a first detection optical path and a second detection optical path. The detection optical system further includes, on the first detection optical path, a first sensor, and on the second detection optical path, a second sensor. A signal processor is provided which, in accordance with at least one of a first signal obtained from the first sensor and a second signal obtained from the second sensor, discriminates defects or defect candidates present on a surface of a sample.

11 Claims, 14 Drawing Sheets

FOREIGN PATENT DOCUMENTS

| | | |
|---|---|---|
| JP | 10-246616 | 9/1998 |
| JP | 2000-105203 | 4/2000 |
| JP | 2000-105203 | 11/2000 |
| JP | 2001-289794 | 10/2001 |
| JP | 2003-130808 | 5/2003 |
| JP | 2003-177102 | 6/2003 |
| JP | 2003/069263 | 8/2003 |
| JP | 2006/501469 | 1/2006 |
| JP | 2006-98156 | 4/2006 |
| JP | 2006-227016 | 8/2006 |

* cited by examiner

APPARATUS FOR INSPECTING DEFECTS

CROSS REFERENCE TO RELATED APPLICATION

This application is a continuation of U.S. application Ser. No. 12/771,216, filed Apr. 30, 2010, now U.S. Pat. No. 8,004,666, which is a continuation of U.S. application Ser. No. 11/936,115, filed Nov. 7, 2007, now U.S. Pat. No. 7,714,997, the contents of which are incorporated herein by reference.

BACKGROUND OF THE INVENTION

The present invention relates to an apparatus and method for inspecting defects, contamination, and other foreign substances present on minute patterns formed on a substrate through a thin-film process represented by a semiconductor manufacturing process and a flat-panel display manufacturing process.

A conventional apparatus for inspecting defects in semiconductors is disclosed in, for example, International Patent Publication WO2003/0069263. The conventional inspection apparatus described in WO2003/0069263 illuminates the surface of a wafer obliquely with laser light, and after the light has been scattered from the wafer surface, captures the scattered light by use of an objective lens disposed above the wafer. The scattered light that has been captured is detected according to the particular scattering angle by a plurality of detectors. Detection images that have thus been obtained are compared with images of adjacent dies in order to detect defects.

Another known apparatus for inspecting defects in semiconductors is disclosed in, for example, JP-A-2000-105203 (Patent Document 2). According to Patent Document 2, during defect inspection of an inspection object (semiconductor wafer) having an array of LSI chips each provided with a register group region and memory block region including an iterative pattern formed thereon, and with a CPU core block region and input/output block region including a non-iterative pattern formed thereon, an optical system for darkfield illumination illuminates the wafer with slit-shaped beams of mutually different wavelengths obliquely from different directions within a horizontal plane, and an optical system for darkfield detection detects defects present on a dielectric film such as an oxide film. It is also described in Patent Document 2 that the optical system for darkfield detection includes an objective lens, a spatial filter formed by a recurrence of an iterative light-shielding pattern, an ND filter, a polarizer, a branching optics (beam splitter) formed to split the beam of light reflected from the inspection object after being passed through the spatial filter, the ND filter, and the polarizer, and increase the intensity of one of the reflected beams branched by the branching optics, to substantially $1/100$ of the intensity of the other reflected beam, and a plurality of image sensors (detectors) each for receiving each reflected beam split by the beam splitter. In addition, it is described in Patent Document 2 that the ND filter, when disposed behind the beam splitter, can conduct independent control of the intensity of each beam of light incident upon two detectors.

SUMMARY OF THE INVENTION

In the above two citations (Documents 1 and 2), however, sufficient consideration has not been given to improving a defect detection ratio by, during defect inspection of a mixed-type wafer (such as system LSI) or other electronic components each inclusive of a memory block formed with a periodic circuit pattern, and of a logic circuit block formed with an irregular circuit pattern (non-periodic circuit pattern), detecting defects with high sensitivity and detecting a wide variety of defect species.

An object of the present invention is to provide a defect inspection apparatus adapted to solve the above problem and to improve a defect detection ratio during defect inspection of a mixed-type wafer (such as system LSI) or the like by detecting defects with high sensitivity and detecting a wide variety of defect species.

In the present invention, a reflecting objective lens free from chromatic aberration is employed to suppress changes in brightness due to multi-wavelength illumination (i.e., illumination with the irradiation light having a plurality of wavelength bands), to provide a clearer view of defects present on a sample, by means of selective wavelength detection in order to improve sensitivity, and to allow one spatial image on the sample to be acquired as different kinds of optical images.

That is to say, one aspect of the present invention is a defect inspection apparatus including:

a darkfield illumination optical system that conducts darkfield illumination upon the surface of a sample with irradiation light having a plurality of wavelength bands;

a darkfield detection optical system that includes a reflecting objective lens for converging the light scattered from the surface of the sample that has been darkfield-illuminated with the irradiation light having the plurality of wavelength bands, and imaging optics for imaging onto a light-receiving surface of an image sensor the scattered light that the reflecting objective lens has converged; and an image processor which, in accordance with an image signal obtained from the image sensor of the darkfield detection optical system, discriminates defects or defect candidates present on the surface of the sample.

Another aspect of the present invention is a defect inspection apparatus including:

a darkfield illumination optical system that conducts darkfield illumination upon the surface of a sample with irradiation light having a plurality of wavelength bands;

a darkfield detection optical system that includes a reflecting objective lens for converging the light scattered from the surface of the sample that has been darkfield-illuminated with the irradiation light having the plurality of wavelength bands, and wavelength selection optics for selecting a wavelength band for the scattered light that has been converged by the reflecting objective lens, and after the wavelength band selection, branching the scattered light into at least a first detection optical path and a second detection optical path, the foregoing darkfield detection optical system further having, on the first detection optical path, first imaging optics for imaging onto a light-receiving surface of a first image sensor the first scattered light having the wavelength band which has been selected by the wavelength selection optics, and the darkfield detection optical system further having, on the second detection optical path, second imaging optics for imaging onto a light-receiving surface of a second image sensor the second scattered light having the wavelength band which has been selected by the wavelength selection optics; and an image processor which, in accordance with an image signal(s) obtained from the first image sensor or/and second image sensor of the darkfield detection optical system, discriminates defects or defect candidates present on the surface of the sample.

Yet another aspect of the present invention is a defect inspection apparatus including:

a darkfield illumination optical system that conducts darkfield illumination upon the surface of a sample with irradiation light having a plurality of wavelength bands;

a darkfield detection optical system that includes a reflecting objective lens for converging the light scattered from the surface of the sample that has been darkfield-illuminated with the irradiation light having the plurality of wavelength bands, and wavelength selection optics for selecting a wavelength band for the scattered light that has been converged by the reflecting objective lens, and after the wavelength band selection, branching the scattered light into at least a first detection optical path and a second detection optical path, the darkfield detection optical system further having, on the first detection optical path, a first spatial filter for optically shielding, of all the first scattered light having the wavelength band which has been selected by the wavelength selection optics, only a diffraction image arising from a periodic circuit pattern formed on the surface of the sample, and first imaging optics for imaging onto a light-receiving surface of a first image sensor the first scattered light that has been passed through the first spatial filter, and the darkfield detection optical system further having, on the second detection optical path, a second spatial filter for optically shielding, of all the second scattered light having the wavelength band which has been selected by the wavelength selection optics, only a region high in an intensity distribution of the scattered light arising from a non-periodic circuit pattern formed on the surface of the sample, and second imaging optics for imaging onto a light-receiving surface of a second image sensor the second scattered light that has been passed through the second spatial filter; and an image processor which, in accordance with a first image signal obtained from the first image sensor of the darkfield detection optical system, or/and a second image signal obtained from the second image sensor, discriminates defects or defect candidates present on the surface of the sample.

In a further aspect of the present invention, the darkfield detection optical system further has a first polarizing filter on the first detection optical path, and a second polarizing filter on the second detection optical path. In a further aspect of the present invention, the darkfield detection optical system further has an ND filter for reduction in intensity of the light, on the first detection optical path or the second detection optical path.

In a further aspect of the present invention, the image processor selects the first image signal or the second image signal, depending upon at least whether the circuit pattern of interest, formed on the surface of the sample, has periodicity, and then discriminates the defects or the defect candidates. In a further aspect of the present invention, the light-receiving surfaces of the first and second image sensors in the darkfield detection optical system are formed into a rectangular shape, and the irradiation light in the darkfield illumination optical system is a slit-shaped beam corresponded to the rectangular field shape of the light-receiving surfaces.

A further aspect of the present invention is a defect inspection apparatus including:

a darkfield illumination optical system that conducts darkfield illumination upon the surface of a sample with irradiation light having a plurality of wavelength bands;

a darkfield detection optical system that includes a reflecting objective lens for converging the light scattered from the surface of the sample that has been darkfield-illuminated with the irradiation light having the plurality of wavelength bands, and branching optics for branching the scattered light that the reflecting objective lens has converged, into at least a first detection optical path and a second detection optical path, the foregoing darkfield detection optical system further having, on the first detection optical path, a first wavelength selection filter for selecting a first wavelength band from a distribution of the scattered light which has been branched by the branching optics, and first imaging optics for imaging onto a light-receiving surface of a first image sensor the first scattered light having the first wavelength band which has been selected by the first wavelength selection filter, and the darkfield detection optical system further having, on the second detection optical path, a second wavelength selection filter for selecting a second wavelength band from the distribution of the scattered light which has been branched by the branching optics, and second imaging optics for imaging onto a light-receiving surface of a second image sensor the second scattered light having the second wavelength band which has been selected by the second wavelength selection filter; and an image processor which, in accordance with a first image signal obtained from the first image sensor of the darkfield detection optical system, or/and a second image signal obtained from the second image sensor, discriminates defects or defect candidates present on the surface of the sample.

A further aspect of the present invention is a defect inspection apparatus including:

a darkfield illumination optical system that conducts darkfield illumination upon the surface of a sample with irradiation light having a plurality of wavelength bands;

a darkfield detection optical system that includes a reflecting objective lens for converging the light scattered from the surface of the sample that has been darkfield-illuminated with the irradiation light having the plurality of wavelength bands, and branching optics for branching the scattered light that the reflecting objective lens has converged, into at least a first detection optical path and a second detection optical path, the foregoing darkfield detection optical system further having, on the first detection optical path, a first wavelength selection filter for selecting a first wavelength band from a distribution of the scattered light which has been branched by the branching optics, a first spatial filter for optically shielding, of all the first scattered light having the first wavelength band which has been selected by the first wavelength selection filter, only a diffraction image arising from a periodic circuit pattern formed on the surface of the sample, and first imaging optics for imaging onto a light-receiving surface of a first image sensor the first scattered light which has been passed through the first spatial filter, and the darkfield detection optical system further having, on the second detection optical path, a second wavelength selection filter for selecting a second wavelength band from the distribution of the scattered light which has been branched by the branching optics, a second spatial filter for optically shielding, of all the second scattered light having the second wavelength band which has been selected by the second wavelength selection filter, only a region high in an intensity distribution of the scattered light arising from a non-periodic circuit pattern formed on the surface of the sample, and second imaging optics for imaging onto a light-receiving surface of a second image sensor the second scattered light which has been passed through the second spatial filter; and an image processor which, in accordance with a first image signal obtained from the first image sensor of the darkfield detection optical system, or/and a second image signal obtained from the second image sensor, discriminates defects or defect candidates present on the surface of the sample.

A further aspect of the present invention is a defect inspection apparatus including:

a darkfield illumination optical system that conducts darkfield illumination upon the surface of a sample with irradiation light having a plurality of wavelength bands;

a darkfield detection optical system that includes a reflecting objective lens for converging the light scattered from the surface of the sample that has been darkfield-illuminated with the irradiation light having the plurality of wavelength bands, and branching optics for branching the scattered light that the reflecting objective lens has converged, into at least a first detection optical path and a second detection optical path, the foregoing darkfield detection optical system further having, on the first detection optical path, a first spatial filter for optically shielding the light diffracted from a periodic circuit pattern formed on the surface of the sample, and first imaging optics for imaging onto a light-receiving surface of a first image sensor the first scattered light which has been passed through the first spatial filter, the foregoing darkfield detection optical system further having, on the second detection optical path, a second spatial filter for optically shielding a region high in an intensity distribution of the scattered light arising from a non-periodic circuit pattern formed on the surface of the sample, and second imaging optics for imaging onto a light-receiving surface of a second image sensor the second scattered light which has been passed through the second spatial filter, and the foregoing darkfield detection optical system further having, on the first detection optical path or the second detection optical path, an ND filter for reduction in intensity of the light; and an image processor which, in accordance with a first image signal obtained from the first image sensor of the darkfield detection optical system, or/and a second image signal obtained from the second image sensor, discriminates defects or defect candidates present on the surface of the sample.

A further aspect of the present invention is a defect inspection apparatus including:

a darkfield illumination optical system which, after rectangularly shaping irradiation light having a plurality of wavelength bands, irradiates the surface of a sample from an oblique direction;

a darkfield detection optical system that includes a reflecting objective lens for converging the light scattered from the surface of the sample that has been darkfield-illuminated with the irradiation light of the plural wavelength bands by the darkfield illumination optical system, and branching optics for branching the scattered light that has been converged by the reflecting objective lens, into at least a first detection optical path and a second detection optical path, the darkfield detection optical system being adapted to cause either a spatial filter or a polarizer, or both thereof, to differ in setting state between the first detection optical path and the second detection optical path such that the scattered beams of light, obtained on the detection optical paths, will differ from each other in characteristics, further has, on the first detection optical path, a first spatial filter and a first polarizer, on the second detection optical path, a second spatial filter and a second polarizer, and on at least either of the first and second detection optical paths, an ND filter, and further has, on the first detection optical path, first imaging optics for imaging onto a light-receiving surface of a first image sensor the first scattered light obtained after being passed through the first spatial filter and the first polarizer, and on the second detection optical path, second imaging optics for imaging onto a light-receiving surface of a second image sensor the second scattered light obtained after being passed through the second spatial filter and the second polarizer; and an image processor which, in accordance with a first image signal obtained from the first image sensor of the darkfield detection optical system, or/and a second image signal obtained from the second image sensor, discriminates defects or defect candidates present on the surface of the sample.

A further aspect of the present invention is a defect inspection apparatus including:

a darkfield illumination optical system that conducts darkfield illumination upon the surface of a sample with an illumination beam of light from an oblique direction;

a darkfield detection optical system with branching optics for branching the converged light into a first detection optical path and a second detection optical path, has, on the first detection optical path formed by the branching optics, a first spatial filter for optically shielding a diffraction image arising from a periodic circuit pattern formed on the surface of the sample, and a first detector for receiving an optical image of the light scattered from the periodic circuit pattern after being passed through the first spatial filter and imaged, and then converting the image into a first image signal, has, on the second detection optical path formed by the branching optics, a second spatial filter for optically shielding, of all the scattered light arising from a non-periodic circuit pattern formed on the surface of the sample, only the scattered light in a region high in intensity distribution, and a second detector for receiving an optical image of the light scattered from the non-periodic circuit pattern after being passed through the second spatial filter and imaged, and then converting the image into a second image signal, and has, on at least either of the first and second detection optical paths, an ND filter for reducing the light in intensity; and an image processor which, in accordance with either a first image signal obtained from the first detector provided on the first detection optical path of the darkfield detection optical system, or a second image signal obtained from the second detector provided on the second detection optical path of the darkfield detection optical system, discriminates defects or defect candidates present on the surface of the sample.

These and other objects, features and advantages of the invention will be apparent from the following more particular description of preferred embodiments of the invention, as illustrated in the accompanying drawings.

BRIEF DESCRIPTION OF THE DRAWINGS

FIG. 5A showing an intensity distribution of scattered light obtained from a non-periodic circuit pattern, FIG. 5B showing a first example of the apertured non-periodic type of spatial filter, and FIG. 5C showing a second example of the apertured non-periodic type of spatial filter;

FIG. 6A showing an example in which a double-refracting material is formed in any one of multiple apertures, and FIG. 6B showing an example in which a material for assigning a phase difference π is disposed;

DETAILED DESCRIPTION OF THE PREFERRED EMBODIMENTS

Hereunder, embodiments of a method and apparatus according to the present invention for inspecting defects, contamination, and other foreign substances present on minute patterns formed on a substrate through a thin-film process will be described using the accompanying drawings.

First Embodiment

Figure 1:
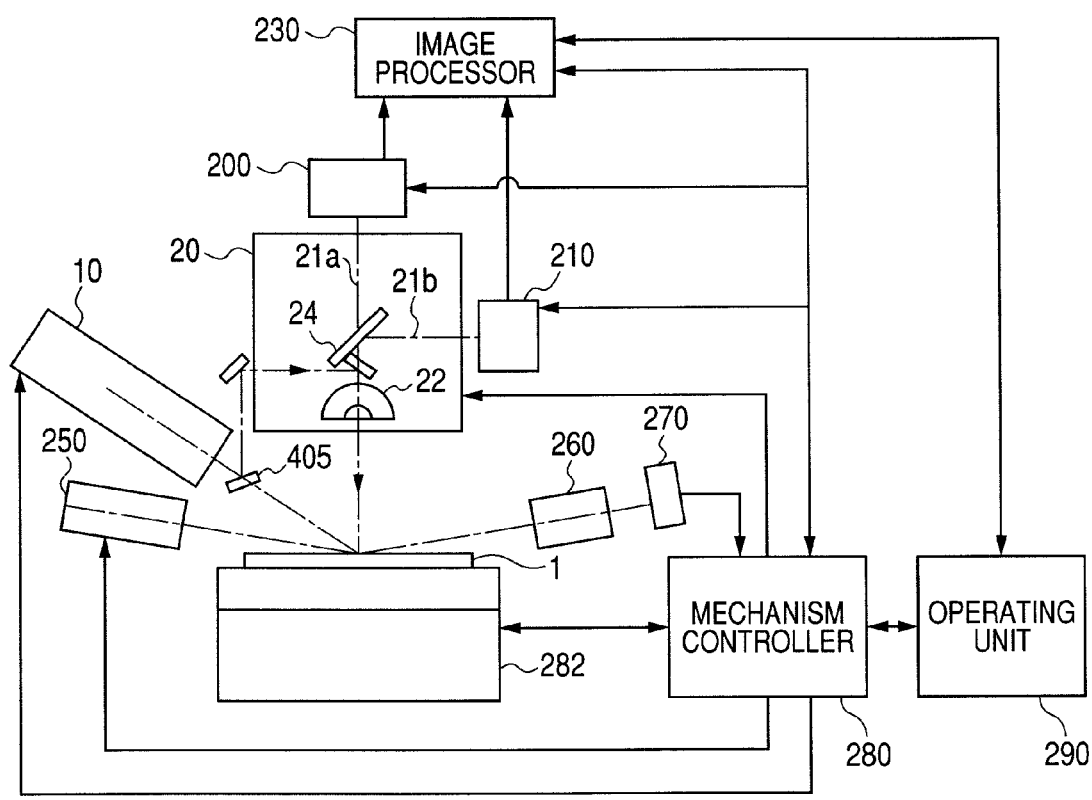
FIG. 1 is a diagram showing a schematic configuration of a defect inspection apparatus of the present invention.
Figure 7:
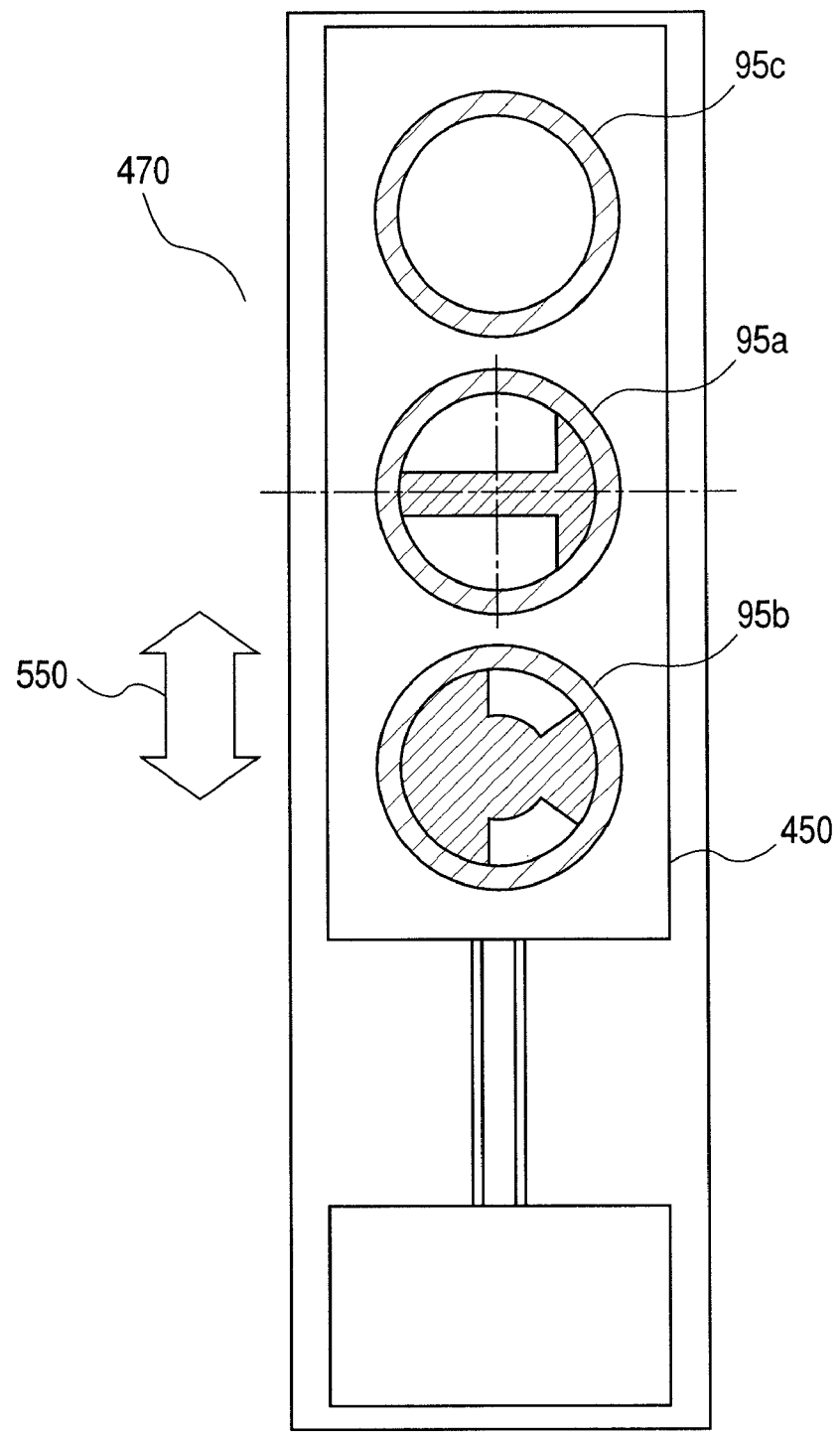
FIG. 7 is a diagram showing an example of a mechanism for switching a spatial filter in the present invention.
Figure 8:
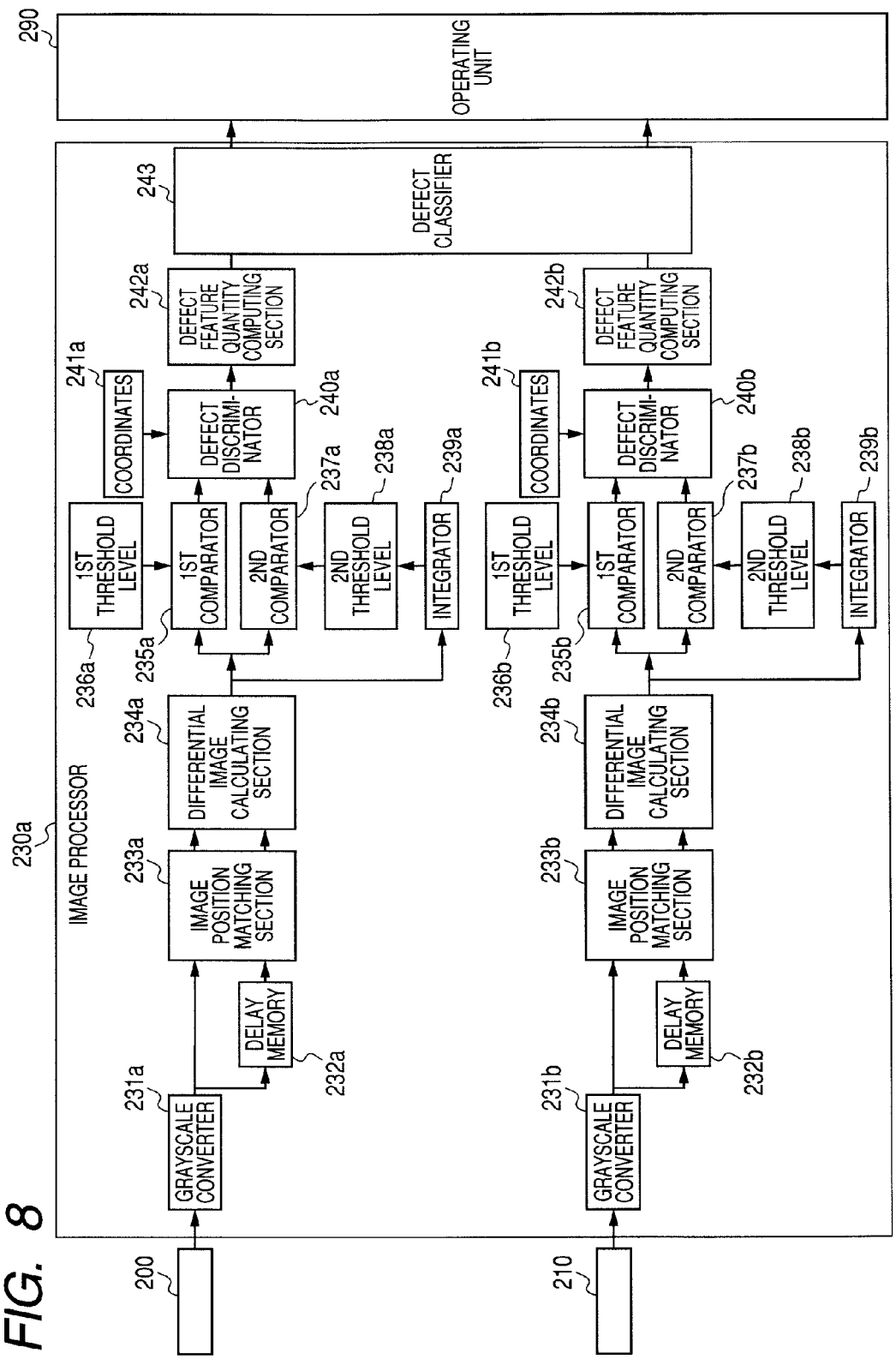
FIG. 8 is a block diagram showing a first example of an image processor used in the present invention.

A schematic configuration of an optical defect inspection apparatus according to the present invention is shown in FIG. 1. A darkfield illumination optical system 10 conducts oblique darkfield illumination upon a wafer (sample) 1 from a normal direction thereof with illumination light of a plurality of wavelengths or a plurality of wavelength bands, through an exterior of a reflecting objective lens. A darkfield detection optical system 20 with a reflecting objective lens 22 free from chromatic aberration captures (converges) the light scattered from the defects or other foreign substances or patterns existing on the wafer (sample) 1. The darkfield detection optical system 20 has a beam splitter 24 to branch a detection optical path into a first detection optical path and a second detection optical path. The beam splitter 24 is either a dichroic mirror for wavelength separation, a polarized beam splitter for polarized beam separation, or a beam splitter for simple branching based on a half-mirror. On the first detection optical path 21a (equivalent to a memory block), the darkfield detection optical system 20 also has a first spatial filter 50 for optically shielding a diffraction image (diffraction pattern) arising from a periodic pattern region formed on the surface of the wafer 1, such as the memory block. On the second detection optical path (equivalent to a logic circuit block) 21b, the darkfield detection optical system 20 has a neutral density (ND) filter 90 to reduce the amount of light. In addition, the darkfield detection optical system 20 has switchable second spatial filters 95a and 95b. The second spatial filters 95a and 95b have a specific aperture shape 95a or 95b, respectively, not such a periodic shape as that of the logic circuit block formed on the surface of the wafer 1. The darkfield detection optical system 20 further has one set of polarizers (polarizing filters), 30 and 35, on the first detection optical path 21a, and one set of polarizers (polarizing filters), 80 and 85, on the second detection optical path 21b. Besides, the darkfield detection optical system 20 has a first image sensor 200 and a second image sensor 210 on image-forming surfaces of the first detection optical path 21a and second detection optical path 21b, respectively. Detection image signals that have been generated by detection with the first and second image sensors 200, 210 are transmitted to an image processor 230. As shown in FIGS. 7 and 8, the image processor 230 conducts position matching between each received detection image signal and, for example, an adjacent image signal (reference image signal), and detects defects or defect candidates by comparing the position-matched image signals. That is to say, the detection image signal obtained from the first image sensor 200 is used to detect the defects or defect candidates that occurred or have occurred in the memory block, and the detection image signal obtained from the second image sensor 210 is used to detect the defects or defect candidates that occurred or have occurred in the logic circuit block.

Although the configuration for oblique illumination is shown in FIG. 1, the inspection apparatus may be constructed to have a mirror 405 on the optical path of the illumination light and bend this optical path so that the wafer 1 is perpendicularly illuminated via an objective lens 22. To conduct darkfield detection under this structure, the detection optical path 21a, 21b or a common optical path needs to have a spatial filter so as to shield regularly reflected light or diffracted light. This spatial filter will be detailed using FIG. 2. It is easily conceivable that an achromatic catadioptric or dioptric objective lens could be used as an alternative for the reflecting objective lens.

Coordinates and sizes of the defects or defect candidates that were detected have been detected in each region by the image processor 230, or image feature quantities of the detected defects or defect candidates, and other defect information are sent to an operating unit 290. The operating unit 290 is a device provided for a person to operate the inspection apparatus. The operating unit 290 is used, for example, to create inspection recipes, specify inspection based on a created recipe, display a map of inspection results, and display the image feature quantities of the detected defects. For example, when inspection is specified from the operating unit 290, an instruction is sent from a mechanism controller 280 to a stage 282 to move the stage 282 to a starting position of the inspection. A distance through which the stage 282 has been moved is sent therefrom to the mechanism controller 280, which then judges whether the wafer 1 has been positioned within a tolerance with respect to the movement distance. If the wafer has been positioned outside the tolerance, feedback control is conducted to position the wafer within the tolerance. Next if the first image sensor 200 and the second image sensor 210 are one-dimensional image sensors (including a time delay integration (TDI) type), an image of the surface of the wafer 1 is acquired while the stage 282 is being moved at a constant speed. For TDI image sensors, since nonuniformity in the speed of the stage 282 causes detection image blurring, speed information on the stage 282 is sent to the mechanism controller 280 to ensure synchronization with vertical transfer timing of the image sensor 200, 210. In addition, warpage of the surface of the wafer 1 or a Z-directional deviation of the stage during movement may cause a position on the surface of the wafer 1 to shift with respect to a focal position of the optical system. Accordingly, for example, a slit image is projected from an auto-focus (AF) illumination system 250 onto the surface of the wafer 1, then the slit image that has reflected is formed by an AF detection system 260, and this slit image is detected by an optical detector 270. Information of the detected slit image is sent to the mechanism controller 280 and height information of the wafer 1 is calculated. Height of the wafer 1 can be detected by calculating a position of the detected slit image. This scheme is an AF scheme generally called an optical lever method. A through-the-lens (TTL) optical lever method, a striped pattern projection method, and the like are known in addition to the AF scheme. If a difference between the focal position of the darkfield detection optical system 20 and the height of the wafer 1 that has been detected using the AF scheme is outside the tolerance, a driving instruction is given from the mechanism controller 280 to a Z-axis actuator of the stage 282 so that the difference falls within the tolerance. This prevents defocusing of the images detected by the first and second image sensors 200, 210.

Figure 2:
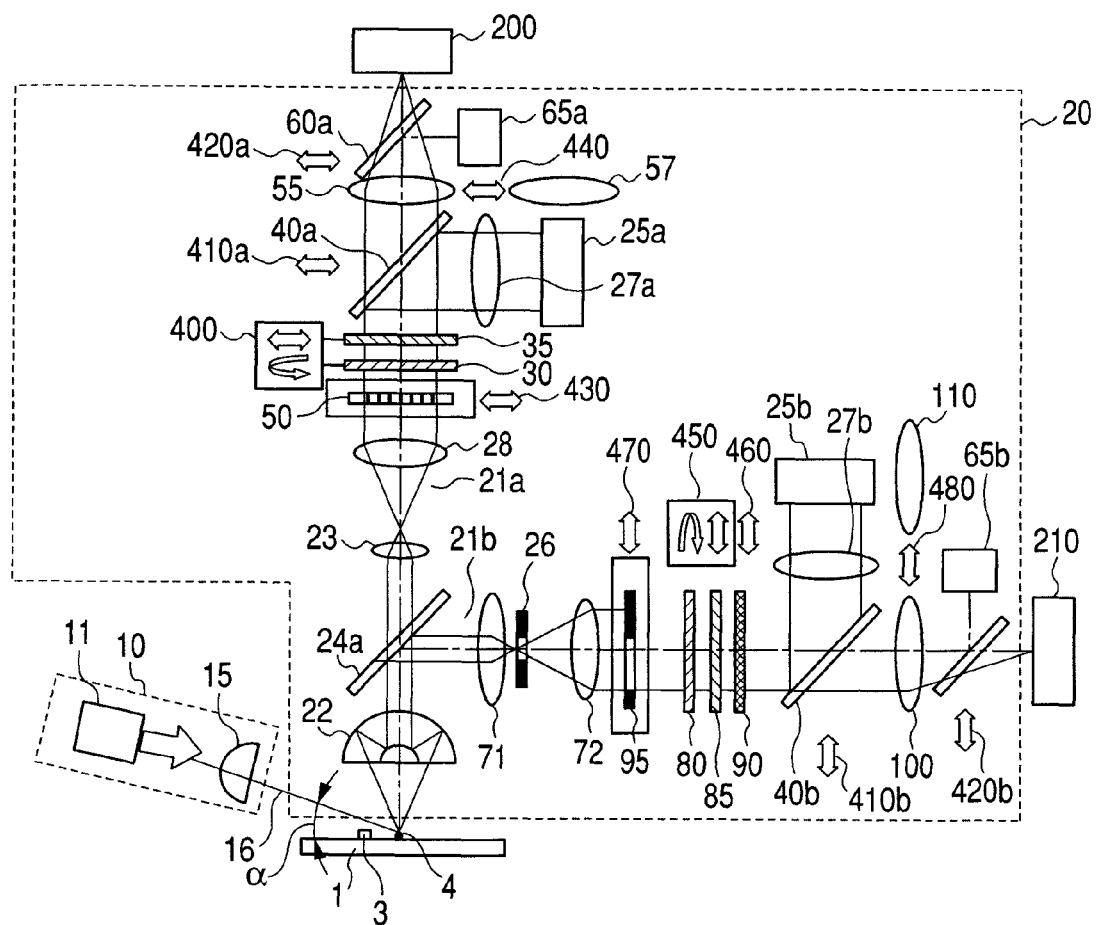
FIG. 2 is a configuration diagram showing an example of an optical system which includes a darkfield illumination optical system and darkfield detection optical system in a defect inspection apparatus of the present invention.

In addition, as shown in FIG. 2, each of the first and second image sensors 200, 210 disposed on the first and second detection optical paths 21a, 21b which were created by the beam splitter 24 detects an image of the same position on the wafer 1, in the darkfield detection optical system 20. For example, if the wafer 1 is a mixed-type wafer (such as system LSI) formed by an array of dies on each of which a memory block with a periodic cell pattern and a logic circuit block with an irregular logic pattern are arranged, a diffracted light pattern (diffraction image) from the memory block with the periodic circuit pattern is, as shown in FIG. 19 of Patent Document 2, shielded by the first spatial filter 50 disposed on the first detection optical path 21a, the first spatial filter 50 being an element constructed by a recurring optical shield. For the image detected by the first image sensor 200, therefore, only the light scattered from a random defect is detected, whereas, since the light scattered from the logic circuit block having an irregular logic pattern formed thereon cannot be shielded using the first spatial filter 50 provided on the first detection optical path 21a, a greater amount of light reaches the first image sensor 200. Accordingly, the above difference in the amount of light detected is corrected by the intensity-reducing ND (Neutral Density) filter 90 disposed on the second detection optical path 21b, and image signals associated with respective regions of both the memory block and the logic circuit block are detected by the first image sensor 200 and the second image sensor 210, in an appropriate dynamic range between the two image sensors. During such detection of the images in the respective regions in the appropriate dynamic range, internal regions of the dies arrayed on the wafer 1 are each split into a plurality of segments with attention focused on the difference in the periodicity of the circuit patterns, and the first image sensor 200 and the second image sensor 210 detect image signals for each segment independently. For example, regarding the memory block and the logic circuit block, the internal regions of each die arrayed on the wafer 1 are each split into two segments on the basis of the difference in the periodicity of the circuit patterns, and image signals associated with each segment are detected by the first image sensor 200 disposed on the first detection optical path 21a, and the second image sensor 210 disposed on the second detection optical path 21b. Although installing the apertured non-periodic spatial filter 95 and the ND filter 90 on the second detection optical path 21b has been described above, if a significantly small aperture size is set for the apertured non-periodic spatial filter 95, the amount of pass-through light detected will decrease, so in this case, the ND filter 90 may be installed on the first detection optical path 21a. In addition, although an example in which one region is split into two segments on the basis of the difference in periodicity has been described above, it is obvious that splitting one region into a larger number of segments (say, 3, 4, or 5) and then detecting respective images with an associated number of image sensors stays within the scope of the present invention. Such splitting into a large number of segments can be accomplished by splitting the detection optical path into a large number of detection optical paths and disposing an image sensor on each detection optical path. Furthermore, for example, a dichroic mirror (wavelength separation optics) for branching based on wavelength separation, a polarized beam splitter for branching based on polarized beam separation, or a beam splitter for simple branching, as with a half-mirror, can be used as a branching method.

Figure 3:
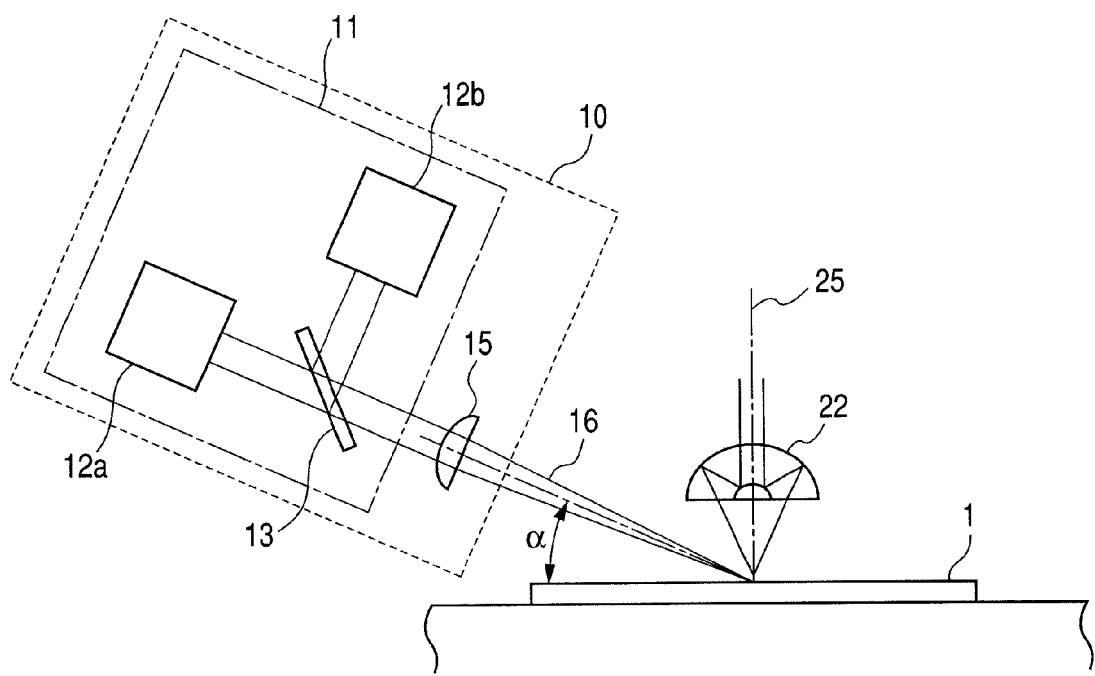
FIG. 3 is a diagram showing a schematic configuration of the darkfield illumination optical system which uses multi-wavelength illumination (i.e., illumination with irradiation light having a plurality of wavelength bands) according to the present invention.

Next, details of the darkfield illumination optical system 10 and the darkfield detection optical system 20 are described below using FIG. 2. An off-axis illumination scheme with an optical axis disposed obliquely with respect to the wafer 1, or a TTL scheme for illuminating the wafer 1 through the reflecting objective lens 22 is available for the darkfield illumination optical system 10. Both schemes can be applied in the present invention. In the present embodiment, however, the off-axis scheme is described below. The optical axis of the darkfield illumination optical system 10 is inclined obliquely with respect to the line normal to the surface of the wafer 1 (with respect to the surface of the wafer 1, formed at an elevation $\alpha$. The light source 11 can be a laser light source or lamp source (such as mercury, mercury xenon, or xenon lamp) that emits illumination light which has a plurality of wavelengths (luminous spectra) or a plurality of wavelength bands. If a laser light source is to be used, this can be a YAG solid-state laser with a second higher-harmonic wavelength of 532 nm, a third higher-harmonic wavelength of 355 nm, a fourth higher-harmonic wavelength of 266 nm, a KrF wavelength of 248 nm, an ArF wavelength of 193 nm, or for stronger laser light, 199 nm. It is possible, as shown in FIG. 3, to provide a plurality of such laser light sources, 12a and 12b, emit laser beams therefrom at the same time, and synthesize the beams into multi-wavelength illumination light including a plurality of wavelengths or wavelength bands, via a dichroic mirror 13. If a lamp light source is to be used, this can be a mercury lamp or a mercury xenon lamp, in which case, multi-wavelength illumination light that includes wavelengths of 578 nm, 547 nm, 436 nm, 405 nm, and 365 nm can be formed as luminous spectra. An alternative lamp light source can be a xenon lamp, in which case, multi-wavelength illumination light with the above luminous spectra superimposed on visible light of a wide band can be formed. As the illumination wavelength is reduced, a greater amount of light will be scattered from minute defects. For this reason, the kind of light applied would be, for example, light of a visible orange-blue band with a wavelength from about 450 nm to about 650 nm (this light may further consist of components with a wavelength band from about 450 nm to about 550 nm, and components with a wavelength band from about 550 nm to about 650 nm), or purple-band UV (ultraviolet) light or DUV (deep ultraviolet) light with a wavelength up to about 440 nm. An example of using a laser light source as the light source 11 in the present embodiment is described below. Multi-wavelength laser light that has been emitted from the laser light source 11 is first refracted in a direction of an angle of incidence by a non-spherical lens or non-spherical mirror (e.g., cylindrical lens) 15 that is a shaping optical section. Next, the surface of the wafer 1 is darkfield-irradiated with the refracted laser light in the form of a linear beam (slit-shaped beam) 16 obtained by shaping original parallel beams of light within a plane orthogonal to the angle of incidence. The linear beam 16 that has been shaped by the shaping optics extends in a planarly crossing direction with respect to the X-direction shown in FIG. 4. This allows the wafer surface to be irradiated linearly (in slit beam form) in association with rectangular fields of the first and second image sensors 200, 210, and multi-wavelength illumination light of high illumination intensity to be irradiated as the linear beam (slit-shaped beam) efficiently in association with the above rectangular (slit-shaped) fields. Accordingly, a plurality of lower-output and less expensive laser light sources 12a, 12b can be used to satisfy the intensity required of the multi-wavelength linear beam, and using these laser light sources 12a, 12b is advantageous for suppressing apparatus costs. In addition, multi-wavelength illumination makes it possible to suppress changes in the amount of light (i.e., changes in brightness) that arise from scattering from the circuit patterns or defects on the wafer 1 due to subtle changes in thickness of a transparent film (such as an oxide film) formed on the wafer.

Next as shown in FIGS. 3 and 4, a defect 4 or circuit pattern 3 on the wafer 1 is darkfield-irradiated with the multi-wavelength linear beam 16 from at least an oblique direction, and of all light that has been scattered or diffracted on the surface of the wafer 1, only light that enters apertures of the reflecting objective lens 22 disposed above the wafer is captured (collected) by the achromatic reflecting objective lens 22. The reflecting objective lens 22 has, for example, a numerical aperture (NA) equal to or greater than 0.6 and less than 1.0. The optical axis 25 of the reflecting objective lens 22 constituting the darkfield detection optical system 20 may be inclined to the normal line of the wafer 1. The light that has been captured by the reflecting objective lens 22 is branched into two optical paths by the beam splitter 24. For example, the beam splitter 24 is either a dichroic mirror 24a for wavelength separation (i.e., wavelength separation optics), a polarized beam splitter 24b (not shown) for polarized beam separation, or a beam splitter for simple branching. If dichroic mirror (wavelength separation optics) 24a is used as the beam splitter (branching optics) 24, the light is separated and branched into wavelengths suitable for the defective material, the object to be inspected. After the light has been branched into two optical paths by the beam splitter 24, functionality equivalent to that of the dichroic mirror (wavelength separation optics) can be implemented by providing a wavelength separation filter on each optical path.

If the object to be inspected is a gate, defects will assume a bright color in a wavelength band from about 400 nm to about 450 nm. If the object to be inspected is aluminum (Al) wiring, this wiring material may have TiN stacked on the surface. The TiN layer has the characteristics that a reflectance thereof increases in a wavelength range of 450-500 nm. Depending on a relationship between a reflectance of the pattern and that of a background (base material), therefore, the wavelengths that allow high-contrast detection of defects may decrease below 450 nm or increase above 500 nm. If the object to be inspected is metallic wiring or the like and the wiring material is copper (Cu), defects will assume a bright color in a wavelength band from about 550 nm to about 700 nm. If the object to be inspected is an element separator, there is no wavelength dependence since the separator is formed up of Si and $SiO_2$. As can be seen from these facts, if spectral and optical constants of the material used for the semiconductor are considered and short-wavelength and long-wavelength sides of spectral characteristics change points at which optical constants (n, k) of the semiconductor material suffer changes are both made usable for illumination, this illumination method will be effective for high-sensitivity inspection of a wide variety of wafers varying in process and structure. That is to say, splitting illumination light into a band of UV light, a blue band of visible light, a green band of visible light, and a red band of visible band, is effective in that this splitting method makes it possible for the inspection apparatus to substantially cover the short-wavelength and long-wavelength sides of the spectral constant and spectral reflectance change points mentioned above.

More specifically, a wavelength band of the visible light obtained from the darkfield illumination optical system 10 is narrowed to about 450-650 nm, for example, and the scattered or diffracted light that has been collected by the reflecting objective lens 22 disposed in the darkfield detection optical system 20 is separated into two wavelength bands (e.g., in order to realize reflection in a yellow-green band of about 550-650 nm and transmission in a blue-purple band of about 450-550 nm) by the wavelength separation optics (dichroic mirror) 24a. The first and second image sensors 200, 210 and the first and second spatial filters 50, 95 are therefore provided for each of the wavelength bands.

Figure 5A:
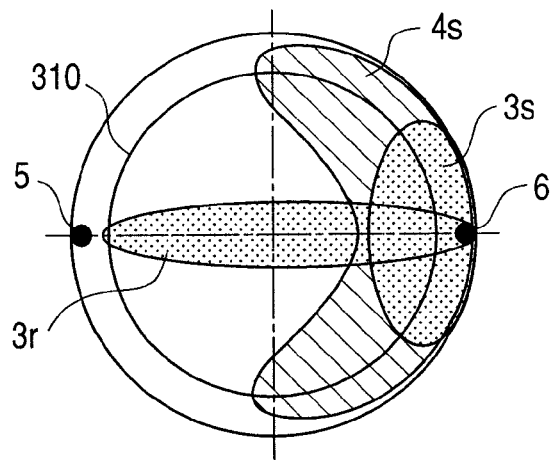
FIGS. 5A, 5B, and 5C are explanatory diagrams that show examples of an apertured non-periodic type of spatial filter formed in the present invention.

Even more specifically, on the first detection optical path 21a formed by passage through the wavelength separation optics 24a, the first spatial filter 50 is disposed on a Fourier transform plane of the wafer image. The first spatial filter 50 can be of a periodic shielding type in which a periodic diffraction image (diffraction pattern) formed on the Fourier transform plane will be shielded according to the periodicity of the pattern formed in, for example, the memory block of the wafer 1. Alternatively, the first spatial filter 50 can be of an apertured non-periodic type having a specific aperture shape, not a periodic pattern shape, to ensure that as shown in FIG. 5A, if the pattern does not have periodicity, a region 3s, 3r that is high in intensity distribution of the light scattered from the logic circuit block or other non-periodic pattern sections is shielded and scattered light of a low region is passed through. The periodic shielding spatial filter is constructed to render the optical shield changeable in pitch so that even if the diffraction image changes in pitch, the diffracted light can be shielded. A plurality of apertured non-periodic spatial filters are provided that each has a plurality of different aperture shapes, as shown in FIG. 5B, 5C or 6A, 6B. The two types of spatial filters are selectively usable via a spatial filter selector 430.

Light that has been passed through the spatial filter 50 can be changed into a specific polarized state by further passing the light through a quarter-wavelength plate 30. This beam of light is further filtered by a polarizer 35. The quarter-wavelength plate 30 and the polarizer 35 are mounted in a polarizer selection mechanism 400 that can be rotated and moved into and out from the optical path. The polarizer selector 400 is adapted to make the wavelength plate 30 and the polarizer 35 rotationally controllable, independently of each other, in accordance with a control command from the mechanism controller 280. The light, after being passed through the polarizers 30, 35, is converged on the first image sensor 200 through an imaging lens 55 to form a darkfield image on the first image sensor 200.

In addition, an imaging lens 57 different from the above imaging lens 55 in focal distance is provided to change a magnification at which the darkfield image will be projected in enlarged form on the first image sensor 200. When the magnification change is conducted, the imaging lens having a focal distance appropriate for the selected magnification is positioned on the optical path by an imaging lens selector 440.

Furthermore, a two-dimensional image sensor 65a is disposed so that a two-dimensional image of the wafer 1 can be detected under a stationary state thereof. The image sensor 65a is mainly used for purposes such as creating an inspection recipe prior to inspection. When the image sensor 65a is unnecessary, the inspection apparatus retreats a beam splitter 60a from the first detection optical path 21a by operating a move-in/out mechanism 420a in accordance with a control command from the mechanism controller 280.

By the way, for a mixed-type wafer (such as system LSI) provided with a memory block in which a periodic circuit pattern is formed, and with a logic circuit block in which an irregular (non-periodic) circuit pattern is formed, since the shape, pitch, and wiring direction of the circuit pattern change according to a particular kind of system LSI, the periodic shielding spatial filter 50 formed by a recurrence of an iterative light-shielding pattern also needs to be changed in shielding position. In addition, since the distribution of scattered light changes according to a particular shape of the defect, the kind of materials used, and the darkfield illumination parameters used, there is a need to change positions of the apertures of the apertured non-periodic spatial filters 50 provide with a plurality of apertures that permit the light from the defect to pass through. For these reasons, to conduct optimal spatial filtering, it is necessary to optimize the shape of the spatial filter 50 according to the particular shape of the circuit pattern 3 or defect 4. Similarly, effectiveness of polarized filtering for permitting only a larger amount of scattered light from the defect 4 to pass through the first image sensor 200 also requires monitoring. For monitoring the diffraction image from the circuit pattern 3 or defect 4 on the first detection optical path 21a, therefore, a move-in/out mechanism 410a positions the beam splitter 40a at rear of the spatial filter 50 and the polarizer 30, 35, on the first detection optical path 21a, and the light to be detected is split by the beam splitter 40a. An imaging lens 27a forms the split light into an image having a relationship conjugate to the spatial filter surface, and a two-dimensional image sensor 25a detects the formed conjugate image. The image that the image sensor 25a has formed, and the darkfield image that the image sensor 200 of the wafer conjugate plane has detected are used to analyze the filtering effect and determine filtering parameters for obtaining an appropriate filter. The beam splitter selector 410a is adapted to move in/out the beam splitter 40a in accordance with a control command from the mechanism controller 280.

For the detection of the light scattered from the defect 4, in particular, a field stop 26 whose field size on the wafer ranges from 1 µm to 10 µm is provided so that only the light exposed to a peripheral region of the defect will be passed through. The field stop 26 provided on the first detection optical path 21a is not shown in the relevant figure. Reference number 28 denotes a collimator lens. Light that the two-dimensional camera 25a has detected via the collimator lens is primarily formed only of the light scattered from the defect region, and this explicitly represents the filtering effect.

Meanwhile, on the second detection optical path 21b formed by the reflection and branching at the wavelength separation filter 24a, the inspection apparatus further includes a second spatial filter 95 (this filter can be of the periodic shielding type or the apertured non-periodic type), a second quarter-wavelength plate 80, a second polarizer 85, second imaging lenses 100 and 110 different from each other in focal distance, and a second image sensor 210. These optical elements are substantially the same as those arranged on the first detection optical path 21b. Between the first detection optical path 21a and the second detection optical path 21b, since a filtering state differs, the amounts of light reaching the image sensors 200, 210 will also differ. When sensitivities of the image sensors 200, 210, gains obtained when sensor output analog signals are converted into digital form, or other parameters are the same, if the above difference in the amount of light is corrected to obtain much the same amount of light between the image sensors 200, 210, dynamic ranges of the image sensors 200, 210 can be effectively used. In order to achieve this, much the same amount of light between the image sensors 200, 210 can be obtained by disposing an ND (neutral density) filter 90 on the optical path larger in the amount of light detected (in the present embodiment, the second detection optical path 21b including the second spatial filter 95 of the apertured non-periodic type, not the periodic shielding type). The spatial filter selector 470, the polarizer rotate and move-in/out mechanism 450, and the imaging lens selector 480 have substantially the same functions as those of the equivalent optical elements disposed on the first detection optical path 21a. The inspection apparatus also has an ND filter selector 460 to conduct adjustments for much the same amount of light detected. The polarizer selector 450 is adapted to make independent rotational control of the wavelength plate 80 and the polarizer 85 each in accordance with the appropriate control command from the mechanism controller 280. Reference numbers 71 and 72 denote a lens and a collimator lens, respectively. Also, a two-dimensional image sensor 65b is disposed so that a two-dimensional image of the wafer 1 can be detected under the stationary state thereof. The image sensor 65b is mainly used for purposes such as creating an inspection recipe prior to inspection. When the image sensor 65b is unnecessary, the inspection apparatus retreats a beam splitter 60b from the second detection optical path 21b by operating a move-in/out mechanism 420b in accordance with a control command from the mechanism controller 280.

Furthermore, to conduct optimal spatial filtering on the second detection optical path 21b, it is also necessary to optimize the shape of the spatial filter 95 according to the particular shape of the circuit pattern 3 or defect 4. Similarly, the effectiveness of polarized filtering for permitting only a larger amount of scattered light from the defect 4 to pass through the image sensor 210 also requires monitoring. For monitoring the diffraction image from the circuit pattern on the second detection optical path 21b, therefore, a move-in/out mechanism 410b positions the beam splitter 40b at the rear of the spatial filter 95 and the polarizer 80, 85, on the second detection optical path 21b, and the light to be detected is split by the beam splitter 40b. An imaging lens 27b forms the split light into an image having a relationship conjugate to the spatial filter surface, and a two-dimensional image sensor 25b detects the formed conjugate image. The beam splitter selector 410b is adapted to move in/out the beam splitter 40b in accordance with a control command from the mechanism controller 280.

The image that the image sensor 25b has formed, and the darkfield image that the image sensor 210 of the wafer conjugate plane has detected are used to analyze the filtering effect and determine filtering parameters for obtaining an appropriate filter. For the detection of the light scattered from the defect 4, in particular, a field stop 26 whose field size on the wafer ranges from 1 µm to 10 µm is provided at a focal position of a lens 71 so that only the light exposed to the peripheral region of the defect will be passed through. Light that the two-dimensional camera 25b has detected is primarily formed only of the light scattered from the defect region, and this explicitly represents the filtering effect.

While an example of bifurcating one detection optical path has been described in the present embodiment, it is obvious that detection of light by a detection system having more detection optical paths also falls within the scope of the present invention.

In addition, any one of the two detection optical paths that have been formed by branching can be selectively used considering several factors. These factors are, for example, the periodicity of the pattern 3 formed on the wafer 1, and the kind of defect to be detected. For example, a periodic pattern region such as the memory block, and a non-periodic region such as the logic circuit block are distinguished during processing, and for the memory block, a defect or a defect candidate is discriminated using the image acquired on the first detection optical path 21a, whereas for the logic circuit block, a defect or a defect candidate is discriminated using the image acquired on the second detection optical path 21b.

For the memory block, since the diffraction image is periodic, the spatial filter 50 with equally pitched linear optical shields is assigned to the first detection optical path 21a. For a non-periodic region such as the logic circuit block, the apertured non-periodic spatial filter 95 is assigned to the second detection optical path 21b. Thus, images advantageous for defect detection can be detected by conducting optimized spatial filtering for each pattern region.

Furthermore, a method of discriminating the detection optical path according to the kind of defect (such as a scratch) is also available. This means that polarized filtering different between the detection optical paths is conducted. Contrast of the defect 4 changes according to a particular direction, shape, and position of the defect 4 (these factors include the difference in position, such as whether the defect is present on or inside a stacked layer), the relationship in position with respect to the peripheral pattern 3, and other factors. Therefore, polarized filtering different between the first detection optical path 21a and the second detection optical path 21b is conducted, the contrast of the defect 4 is enhanced on either detection optical path, and a capturing ratio of the defect 4 existing on the wafer 1 is raised through the reflecting objective lens 22. The methods of filtering setup for the two detection optical paths according to the periodicity of the pattern 3 and the kind of defect have been set forth above, but a setting method consisting of a combination of the above methods is also usable.

When a polarized beam splitter 24b (not shown) is to be used as the beam splitter 24 for detection optical path branching in the darkfield detection optical system 20, the darkfield illumination optical system 10 needs to have, between the dichroic mirror 13 and the cylindrical lens 15, a half-wavelength plate (not shown) for changing a polarizing direction, and a quarter-wavelength plate (not shown) for transforming the beam into a circularly polarized beam or an elliptically polarized beam. The darkfield illumination optical system 10 also needs to irradiate the surface of the wafer 1 with a multi-wavelength S-polarized, P-polarized, or elliptically polarized linear beam (including a circularly polarized beam whose ellipticity is 1) obliquely from the normal direction of the wafer 1. As a result, the scattered or diffracted light obtained from the wafer 1 can be converged upon the reflecting objective lens 22, and then the converged light can be separated into, for example, an S-polarized beam and a P-polarized beam via the foregoing polarized beam splitter (not shown) and branched into the first detection optical path 21a and the second detection optical path 21b.

For defect or defect candidate discrimination, the two images of one space that have been detected by the two image sensors, 200 and 210, are also usable to discriminate the defect or the defect candidate 4. Additionally, since using the two images of the same space allows a greater amount of information on the defect 4 to be obtained, the two images are likely to be utilizable for classifying the defect 4 according to, for example, criticality of the device, the position of the defect (whether the defect is present on a top layer or inside a layer), or a size of the defect, as well as for discriminating the defect or the defect candidate. These also lie within the scope of the present invention.

Figure 14:
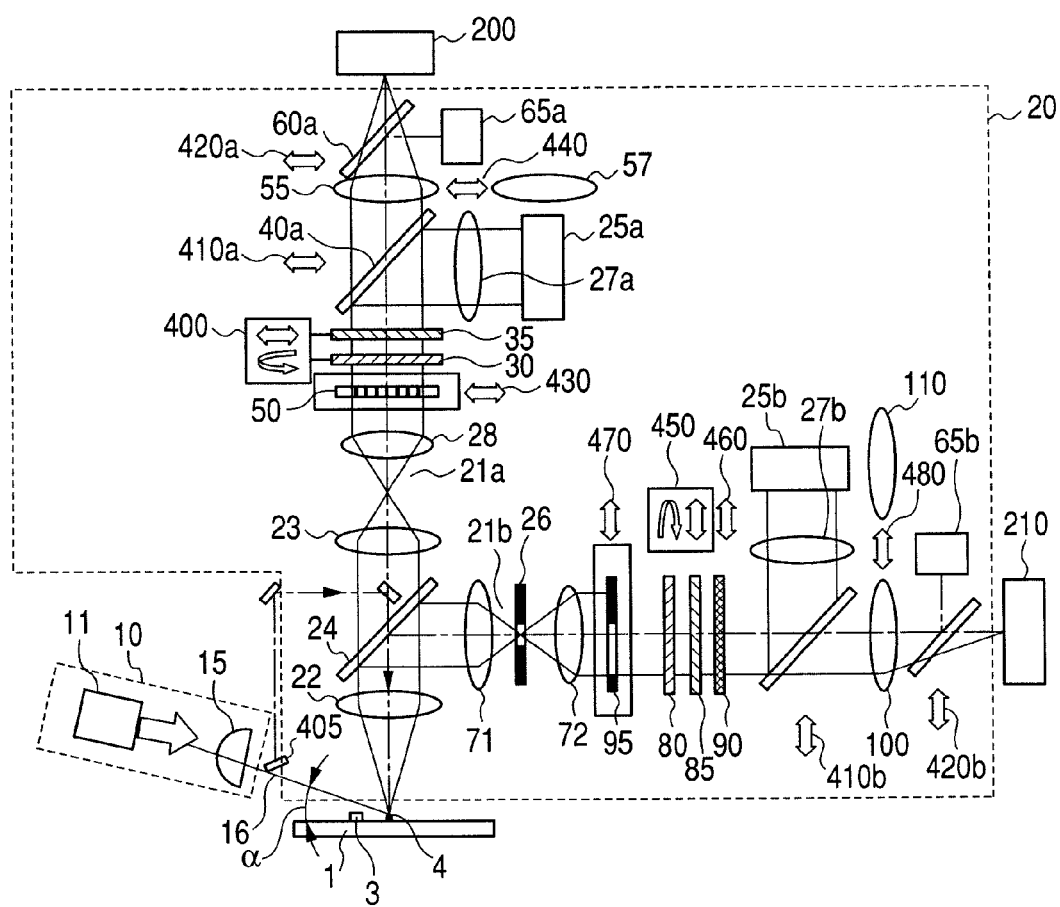
FIG. 14 is a configuration diagram showing another example of an optical system which includes a darkfield illumination optical system and darkfield detection optical system in a defect inspection apparatus of the present invention.

In another example, as shown in FIG. 14, the first image sensor 200 and second image sensor 210 disposed on the first detection optical path 21a and second detection optical path 21b, respectively, created by the beam splitter 24 in the darkfield detection optical system 20, detect an image of the same position on the wafer 1. For example, if the wafer 1 is a mixed-type wafer (such as system LSI) provided with a memory block in which a periodic cell pattern is formed, and with a logic circuit block in which an irregular logic pattern is formed, a diffraction-light pattern (diffraction-light fringe) from the memory block having a periodic cell pattern formed thereon is shielded by the first spatial filter 50 of an iterative shielding pattern shape, disposed on the first detection optical path 21a created by the beam splitter 24 in the darkfield detection optical system 20. For the image detected by the first image sensor 200, therefore, only the light scattered from a random defect is detected, whereas, since the light scattered from the logic circuit block having an irregular logic pattern formed thereon cannot be shielded using the first spatial filter 50 such as the memory block, a greater amount of light reaches the first image sensor 200. Accordingly, the difference in the amount of light detected is corrected by the intensity-reducing ND filter 90 disposed on the second detection optical path 21b created by the beam splitter 24, and image signals associated with the respective regions of both the memory block and the logic circuit block are detected by the first image sensor 200 and the second image sensor 210, in the appropriate dynamic range between the two image sensors. During such detection of the images in the respective regions in the appropriate dynamic range, the internal regions of the dies arrayed on the wafer 1 are each split into a plurality of segments with attention focused on the periodicity and non-periodicity of the circuit patterns, and the first image sensor 200 and the second image sensor 210 detect image signals for each segment independently. Although an example in which one region is split into two segments with attention focused on the periodicity and non-periodicity of the circuit patterns has been described above, it is obvious that splitting one region into a larger number of segments (say, 3, 4, or 5) and then detecting respective images with an associated number of image sensors stays within the scope of the present invention. Such splitting into a large number of segments can be accomplished by splitting the detection optical path into a large number of detection optical paths and disposing an image sensor on each detection optical path. In addition, although installing the apertured non-periodic spatial filter 95 and the ND filter 90 on the second detection optical path 21b has been described above, if a significantly small aperture size is set for the apertured non-periodic spatial filter 95, the amount of pass-through light detected will decrease, so in this case, the ND filter 90 may be installed on the first detection optical path 21a.

Furthermore, if the first image sensor 200 and the second image sensor 210 are each constructed using TDI sensors, an appropriate brightness level of an image signal can be obtained in both the memory block and the logic circuit block by changing independently the number of first TDI sensor stacking stages (i.e., changing a stacking time) and that of second TDI sensor stacking stages, for the memory block and the logic circuit block each.

Next, details of the darkfield illumination optical system 10 and darkfield detection optical system 20 in the present embodiment are described below using FIG. 2. The off-axis illumination scheme with an optical axis disposed obliquely with respect to the wafer 1, or the TTL scheme for illuminating the wafer 1 through the reflecting objective lens 22 is available to dispose the darkfield illumination optical system 10. Both schemes can be applied to the darkfield illumination optical system 10. In the present embodiment, however, the disposition with the off-axis scheme is described below. The optical axis of the darkfield illumination optical system 10 is inclined obliquely with respect to the line normal to the surface of the wafer 1. The light source 11 can be a laser light source or lamp source (such as mercury, mercury xenon, or xenon lamp) that emits illumination light which has a plurality of wavelengths (luminous spectra) or a plurality of wavelength bands. Since reduction in illumination wavelength increases the amount of light scattered, UV (ultraviolet) light or DUV (deep ultraviolet) light would be usable. If a laser light source is to be used, this can be a YAG solid-state laser with a second higher-harmonic wavelength of 532 nm, a third higher-harmonic wavelength of 355 nm, a fourth higher-harmonic wavelength of 266 nm, a KrF wavelength of 248 nm, an ArF wavelength of 193 nm, or for stronger laser light, 199 nm. It is possible, as shown in FIG. 3, to provide a plurality of such laser light sources, 12a and 12b, emit laser beams therefrom at the same time, and synthesize the beams into multi-wavelength illumination light including a plurality of wavelengths or wavelength bands, via a dichroic mirror 13. If a lamp light source is to be used, this can be a mercury lamp or a mercury xenon lamp, in which case, multi-wavelength illumination light that includes wavelengths of 578 nm, 547 nm, 436 nm, 405 nm, and 365 nm can be formed as luminous spectra. An alternative lamp light source can be a xenon lamp, in which case, multi-wavelength illumination light with the above luminous spectra superimposed on visible light of a wide band can be formed. As the illumination wavelength is reduced, a greater amount of light will be scattered from minute defects. For this reason, the kind of light applied would be, for example, light of an orange-blue band with a wavelength from about 450 nm to about 650 nm, or purple-band UV (ultraviolet) light or DUV (deep ultraviolet) light with a wavelength up to about 440 nm. An example of using a laser light source as the light source 11 in the present embodiment is described below. Multi-wavelength laser light that has been emitted from the laser light source 11 is first refracted in the direction of an angle of incidence by a non-spherical lens or non-spherical mirror (e.g., cylindrical lens) 15 that is a shaping optical section. Next, the surface of the wafer 1 is darkfield-irradiated with the refracted laser light in the form of a linear beam (slit-shaped beam) 16 obtained by shaping original parallel beams of light within a plane orthogonal to the angle of incidence. The linear beam 16 that has been shaped by the shaping optics extends in a planarly crossing direction with respect to the X-direction shown in FIG. 4. At this time, the stage 282 provided with the wafer 1 is moved to X-direction. This allows the wafer surface to be irradiated linearly (in slit beam form) in association with the rectangular fields of the first and second image sensors 200, 210, and multi-wavelength illumination light of high illumination intensity to be irradiated as the linear beam (slit-shaped beam) efficiently in association with the above rectangular (slit-shaped) fields. Accordingly, a plurality of lower-output and less expensive laser light sources 12a, 12b can be used to satisfy the intensity required of the multi-wavelength linear beam, and using these laser light sources 12a, 12b is advantageous for suppressing apparatus costs. In addition, multi-wavelength illumination makes it possible to suppress changes in the amount of light (i.e., changes in brightness) that arise from scattering from the circuit patterns or defects on the wafer 1 due to subtle changes in the thickness of the transparent film (such as oxide film) formed on the wafer.

Next as shown in FIG. 4, a defect 4 or circuit pattern 3 is darkfield-irradiated with the multi-wavelength linear beam 16 from at least an oblique direction, and of all light that has been scattered or diffracted on the surface of the wafer 1, only light that enters the apertures of the reflecting objective lens 22 disposed above the wafer is captured (collected) by the achromatic reflecting objective lens 22. The captured light is branched into two optical paths, 21a and 21b, by the beam splitter (branching optics) 24.

On the first detection optical path 21a formed by the beam splitter 24, the first spatial filter 50 is disposed on a Fourier transform plane of the wafer image. The first spatial filter 50 can be of the periodic shielding type in which a periodic diffraction image (diffraction pattern) formed on the Fourier transform plane will be shielded according to the periodicity of the circuit pattern formed on the wafer 1. Alternatively, the first spatial filter 50 can be of the apertured non-periodic type having a specific aperture shape, not a periodic pattern shape, as shown in FIG. 5B, 5C or 6A, 6B. The periodic shielding spatial filter is constructed to render the optical shield changeable in pitch so that even if the diffraction image changes in pitch, the diffracted light can be shielded. A plurality of apertured non-periodic spatial filters are provided that each has a plurality of different aperture shapes, as shown in FIG. 5B, 5C or 6A, 6B. The two types of spatial filters are selectively usable via a spatial filter selector 430. Light that has been passed through the spatial filter 50 can be changed into a specific polarized state by further passing the light through a first quarter-wavelength plate 30. This beam of light is further filtered by a first polarizer 35. The first quarter-wavelength plate 30 and the first polarizer 35 are mounted in a polarizer selection mechanism 400 that can be rotated and moved into and out from the optical path. The light, after being passed through the first polarizers 30, 35, is converged on the first image sensor 200 through a first imaging lens 55 to form a darkfield image on the first image sensor 200. In addition, an imaging lens 57 different from the above imaging lens 55 in focal distance is provided to change a magnification at which the darkfield image will be projected in enlarged form on the first image sensor 200. When the magnification change is conducted, the first imaging lens having a focal distance appropriate for the selected magnification is positioned on the first detection optical path 21a by an imaging lens selector 440. Furthermore, a two-dimensional image sensor 65a is disposed so that a two-dimensional image of the wafer 1 can be detected under a stationary state thereof. The image sensor 65a is mainly used for purposes such as creating an inspection recipe prior to inspection. When the image sensor 65a is unnecessary, the inspection apparatus retreats a beam splitter 60a from the first detection optical path 21a by operating a move-in/out mechanism 420a.

Figure 4A:
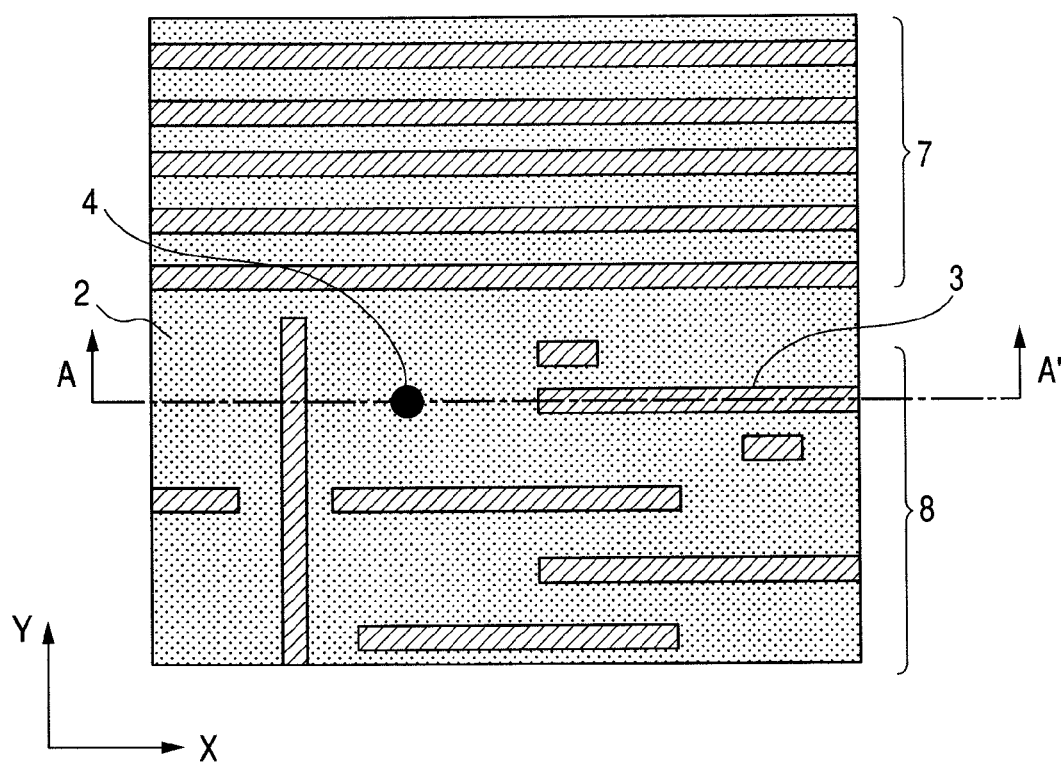
FIG. 4 is a view that shows the surface and section A-A' of a mixed-type wafer to be inspected according to the present invention.
Figure 4B:
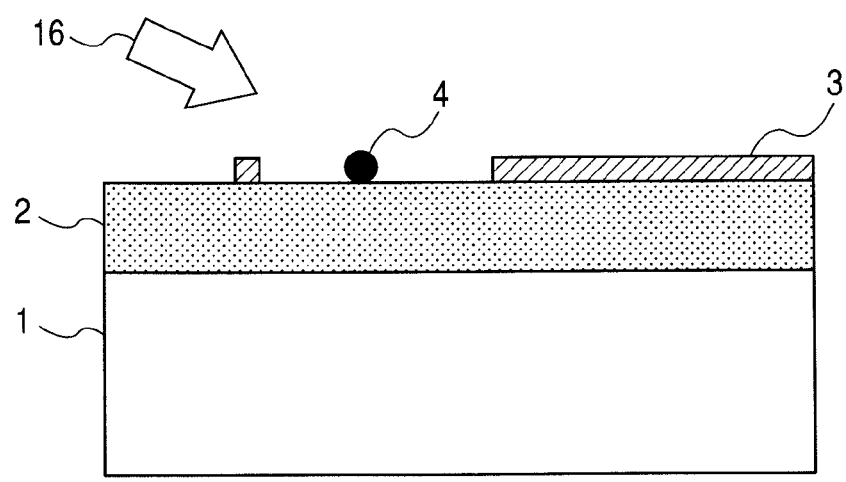

Next, a method of discriminating the two detection optical paths, 21a and 21b, according to periodicity of circuit patterns 3 is described below. A plan view of the circuit patterns 3 formed in a periodic wiring (memory cell) region 7 sectionalized as the memory block in each die arrayed on the wafer 1, and in a non-periodic wiring region 8 sectionalized as the logic circuit block, is shown in FIG. 4A. In this model, each circuit pattern 3 is present on an oxide film, such as $SiO_2$, that is formed as an interlayer dielectric film. The circuit pattern 3 is sectionalized into, for example, the periodic wiring (memory cell) region 7 and the non-periodic wiring region 8. This model also assumes that a defect 4 is present on the oxide film. A sectional view of section A-A' through the non-periodic circuit pattern region 8 is shown in FIG. 4B. On the wafer 1 is formed a transistor (not shown), on which the oxide film 2 is further formed, and on which film is formed a metallic wiring pattern 3 (e.g., tungsten, copper, aluminum, or the like). The pattern 3 is wired so as to be orthogonal primarily to another pattern, and parallel to an X- or Y-direction.

Next, image detection in the sectionalized periodic circuit pattern region 7 is described below. In the periodic circuit pattern region 7 such as the memory block, an image signal is detected primarily on the first detection optical path 21a shown in FIG. 2. The optical shield of the first spatial filter 50 assigned to the first detection optical path 21a is a periodic shielding type of linear spatial filter having equally pitched shielding portions to shield the diffraction image of the circuit pattern.

Figure 5B:
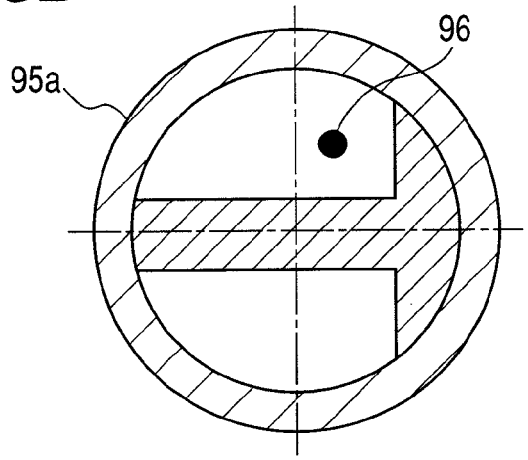

Next, image detection in the sectionalized non-periodic circuit pattern region 8 is described below. Distribution diagrams of the light scattered from the circuit pattern 3 and defect 4 in the non-periodic circuit pattern region 8 (such as the logic circuit block) during oblique illumination (darkfield illumination) of the wafer 1 are shown in FIGS. 5A to 5C.

FIG. 5A is a plan view of the Fourier transform plane in the darkfield detection optical system 20, and a schematic distribution diagram of the light scattered from the circuit pattern 3 and defect 4 in the non-periodic circuit pattern region 8. A circle 310 denotes an actual NA of the reflecting objective lens 22, and the NA shown in the present example is 0.8. A center of this circle is an arrival position of the light which propagates in parallel with respect to the normal line of the wafer surface. At this time, the wafer surface is obliquely irradiated with illumination light 16 from a point 5 outside the reflecting objective lens 22, in the form of a slit-shaped beam extending planarly in an crossing direction with respect to an X-direction, and the 0th-order light that has regularly reflected on the surface of the wafer 1 reaches a point 6 symmetrical with respect to a central portion of the NA. In FIG. 5A showing the light scattered or diffracted from the circuit pattern 3 in the non-periodic circuit pattern region 8, the light scattered or diffracted from the circuit pattern 3 in the circuit pattern region 8 parallel to a Y-direction is, as denoted by reference number 3r, collected mainly on a plane of incidence that is relatively parallel to the Y-direction (although the light scattered from the pattern also propagates into other regions, description of this light is omitted herein). The amounts of light scattered or diffracted from corners of the circuit pattern 3 and from the circuit pattern 3 parallel to the X-direction become relatively high at a peripheral region 3s of the 0th-order diffracted light (regularly reflected light) 6. A distribution 4s of the light scattered from the defect 4 indicates a model in which the light is collected mainly at a peripheral NA portion of forward scattering. To obtain a high-contrast darkfield defect detection image advantageous for defect detection, it is ideal that only the light scattered from the defect 4 should be detected by shielding the light scattered or diffracted from the normal circuit pattern 3 in the non-periodic region. Accordingly, for such scattered-beam distribution as in FIG. 5A, it is effective to dispose a second spatial filter 95 having an aperture 96 in a region substantially free from the light scattered from the normal circuit pattern 3 in the non-periodic circuit pattern region, and exposed to a large amount of light scattered from the defect. In the example of FIG. 5B, the region exposed to a large amount of light scattered from the circuit pattern 3 is shielded by an optical shield 95a, and other regions are formed using the aperture 96.

Figure 5C:
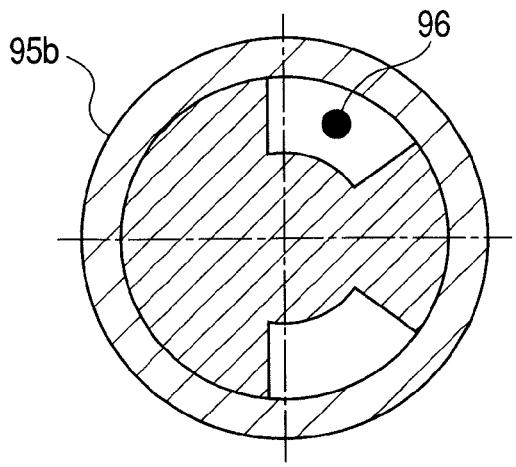

In the example of FIG. 5C, the aperture 96 is formed only in a region substantially free from the light scattered from the normal circuit pattern 3 in the non-periodic circuit pattern region, and exposed to a large amount of light scattered from the defect, and other regions are formed using an optical shield 95b. Distributions of these beams of light change according to not only the shape, direction, and dimensions of the normal circuit pattern 3 in the non-periodic region, but also the kind, position, size, and other factors of defect. Accordingly, the second spatial filter 95 is desirably provided in a plurality of places in the optical system so that an aperture shape of a spatial filter advantageous for inspection can be selected from the spatial filters provided for different structures of wafers 1 to be inspected, for different circuit patterns 3, and for different kinds of defects 4.

Figure 6A:
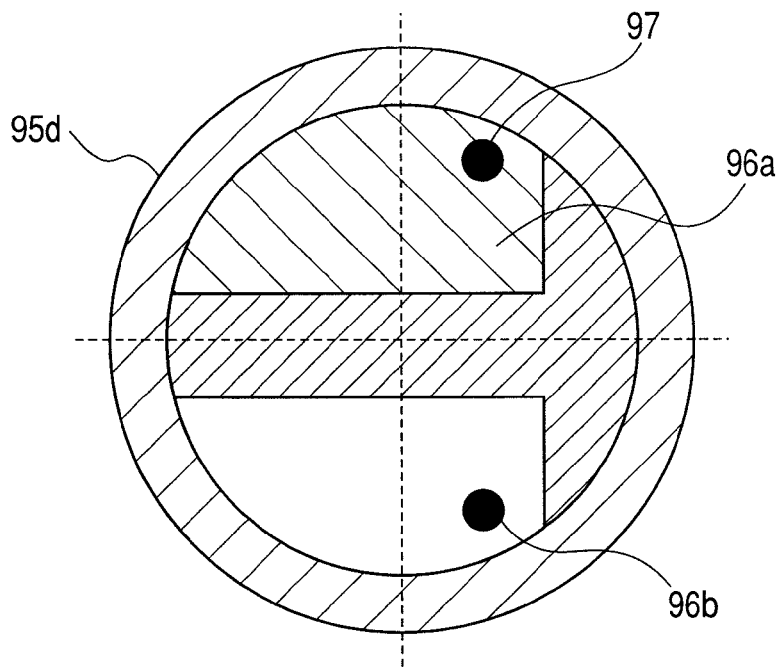
FIGS. 6A and 6B are diagrams that show other examples of the apertured non-periodic type of spatial filter formed in the present invention.

Next, a modification of a second spatial filter 95 is described below using FIG. 6. During darkfield illumination of a wafer 1 with polarized light (e.g., S-polarized light, P-polarized light, and clockwise or counterclockwise circularly polarized light, or P-polarization/S-polarization mixed light with an optical path difference greater than a coherent distance), the light scattered from the circuit pattern 3 and the defect 4 also exhibits polarization characteristics. These polarization characteristics may differ according to the particular scattering direction, and when this property is utilized, the light scattered from the circuit pattern 3 can be processed by polarized filtering, and thus a relatively large amount of light scattered from the defect 4 can be detected. For these reasons, the spatial filter 95d shown in FIG. 6A has, at one aperture 96a, a half-wave film rotating a vibration plane of the polarized light, a film causing a phase difference of a quarter wavelength, or any other double refractor 97, and at another aperture 96b, does not have a phase-difference film. After the light has been passed through such a spatial filter 95a, only a specific polarized beam is passed through via a polarizer 85 to form a darkfield image. The contrast of the defect can thus be further enhanced.

Figure 6B:
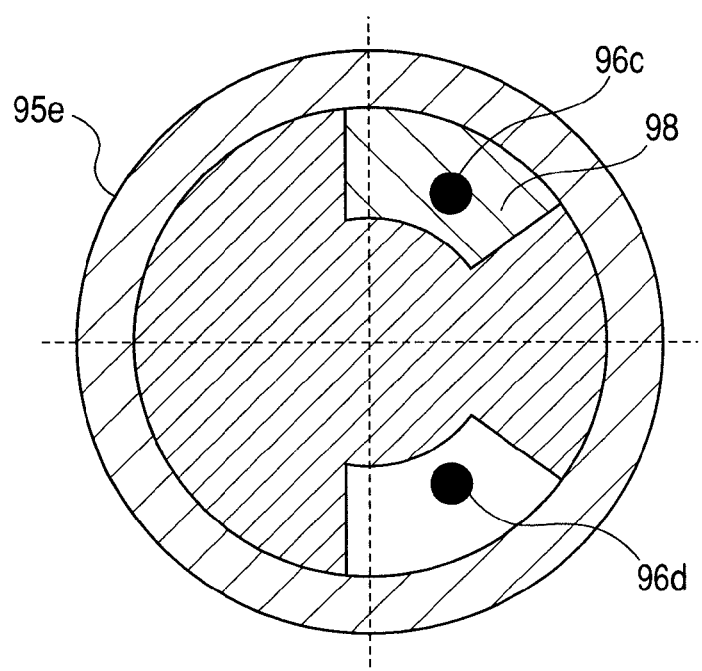

The spatial filter 95e shown in FIG. 6B may not use a double refractor. Instead, the spatial filter 95e may use a method of reducing the intensity of the light from the pattern by utilizing the phase difference between the light passed through an aperture 96c and the light passed through an aperture 96d. The spatial filter 95e uses a material 98, instead of the above double refractor, at the aperture 96c in order to provide the phase difference π.

Although an example of an apertured non-periodic spatial filter 95e with two apertures has been described above, if a larger number of apertures are necessary, it is effective to dispose a double-refractor or a phase difference film (negligibly small in double-refracting performance) considering a phase state and the differences in polarizing characteristics between the defect 4 and the circuit pattern 3 extending through each aperture. It is also effective to combine a double-refractor and a phase difference film.

Next, a selector 470 that selects any one of different multiple spatial filters 95a to 95e is described below using FIG. 7. The selector 470 is constructed so as to be able to select, for example, a linear movement or rotary movement of a stage 450 having the multiple spatial filters 95a to 95e arrayed thereon (only the filters 95a to 95c are shown in FIG. 7). The linear movement or rotary movement 550 of the stage 450 is selected in accordance with a control command from the mechanism controller 280. That is to say, the selector 470 is adapted to selectively set an optimal (e.g., apertured) non-periodic spatial filter according to specifications of the wafer 1 to be inspected. As with the spatial filter selector 470, the spatial filter selector 430 is adapted to selectively set an optimal periodic shielding spatial filter (e.g., one with optical shields arrayed at spatial intervals) according to the specifications of the wafer 1 to be inspected. The selection of the optimal filter is based on a control command from the mechanism controller 280.

It is possible, as described above, to set the apertured non-periodic type of spatial filter as the first spatial filer 50.

As set forth above, according to the first embodiment of the present invention, the adoption of the reflecting objective lens 22 as an objective lens makes it possible, during darkfield detection based on darkfield illumination, to prevent chromatic aberration, to suppress changes in brightness due to multi-wavelength illumination, to acquire a clear defect image signal from, for example, the first and second image sensors 200, 210 each by selecting the appropriate wavelength, and to optimize, by wavelength separation in the darkfield detection optical system, the amount of light detected on the memory block and the logic circuit block.

Defect discrimination by an image processor 230a, based on mutually different kinds of images acquired by the image sensors 200 and 210 on the two detection optical paths, 21a and 21b, is next described below using FIG. 8. The description given here relates to detecting images on the first detection optical path 21a and second detection optical path 21b described using FIG. 2, and to a process flow of the defect discrimination by the image sensor 230a. Since resolution of the brightness of the images detected by the first image sensor 200 and the second image sensor 210 is expressed in 1,024 grayscale levels, the grayscale levels of the image signals detected by the image sensors 200, 210 are converted into 256 grayscale levels when the images undergo processing by grayscale converters 231a, 231b. Linear or non-linear brightness conversion characteristics can be selected when the grayscale conversions are conducted.

The following describes a process flow relating to the image signal f1 detected by the first image sensor 200, and that of the image signal f2 detected by the second image sensor 210. That is to say, the detected image signal f1, f2 obtained by conducting a grayscale level conversion into 256 grayscale levels of brightness information is sent to both an image position-matching section 233a, 233b and a delay memory 232a, 232b. Before the detected image signal that has been sent to the delay memory 232a, 232b is further sent to the image position-matching section 233a, 233b, a reference image signal g1, g2 is created with a time-lag equivalent to, for example, an arrayal pitch of the dies on which the same pattern is formed. This time-lag is provided for reasons associated with design. Accordingly, the real-time detected image signal f1, f2 and the reference image signal g1, g2 relating to an adjacent die, for example, are sent to the image position-matching section 233a, 233b, in which the two image signals are then matched in position and a differential image obtained by position matching of the two image signals is calculated by a differential image calculating section 234a, 234b. The calculated differential image next undergoes two systems of threshold level processing. A first comparator 235a, 235b uses a previously set constant threshold level 236a, 236b to conduct a first threshold level discrimination against an absolute value of the differential image obtained from the differential image calculating section 234a, 234b, and image feature quantities (brightness, size, and other information) in the region of defect candidates exceeding the threshold level are sent to a defect discriminator 240a, 240b. Also, a second threshold level processor (integrator) 239a, 239b derives information, such as variations in internal brightness of the memory region, from a plurality of differential images detected, for example, in the memory region and the logic circuit region, and then generates a second threshold level 238a, 238b based on the variations. The second comparator 237a, 237b conducts a second threshold level discrimination using the second threshold level 238a, 238b generated above for the absolute value of the above differential image. The second threshold level becomes a floating threshold level. As with the first threshold level, image feature quantities in the region of defect candidates exceeding the floating threshold level are sent to the defect discriminator 240a, 240b. The image feature quantities that have been sent from the two systems are next used for the defect discriminators 240a, 240b to conduct synthetic defect discriminations, for example, in the memory block region and the logic circuit block region. At this time, since significant nonuniformity in brightness tends to exist for a specific pattern, a normal section may be mis-discriminated as a defective. By utilizing the fact that the mis-discrimination easily occurs with a specific pattern, the inspection apparatus assigns coordinate information 241a, 241b of the wafer to the defect discriminator 240a, 240b, and sets up a flag to indicate that for the region in which the mis-discrimination is prone to occur, even if the above first or second threshold level is exceeded, the corresponding section will be excluded from the defect discrimination or the discrimination itself is most likely to result in an error. After the setup of the flag, the coordinate information is sent to a defect feature quantity computing section 242a, 242b. The defect feature quantity computing section 242a, 242b uses detected images to calculate the feature quantities of defective sections even more closely than for the image feature quantities that have been sent to the comparator set 235a, 237a or 235b, 237b.

As set forth above, image processing is conducted upon the image signals f1, f2 that have been detected by the first and second image sensors 200, 210, image feature quantities of defective sections, for example, in the memory block region, and feature quantities of defective sections, for example, in the logic circuit block region, are calculated, and calculation results are input to a defect classifier 243.

The defect classifier 243 classifies defects according to, for example, the image feature quantities of internal defective sections of the memory block, obtained from the defect feature computing section 242a on the basis of the defect image signal detected by the first image sensor 200. The defect classifier 243 also classifies defects according to, for example, the image feature quantities of internal defective sections of the logic circuit block, obtained from the defect feature computing section 242b on the basis of the defect image signal detected by the second image sensor 210. The defect classification results, coordinate information, image feature quantities, and other information that have been obtained by the defect classifier 243 are output to a display device (or the like) provided at the operating unit 290. The operator can visually confirm the output information, and the output information is further sent to a host system (not shown) that is undertaking LSI-manufacturing process control.

Figure 9:
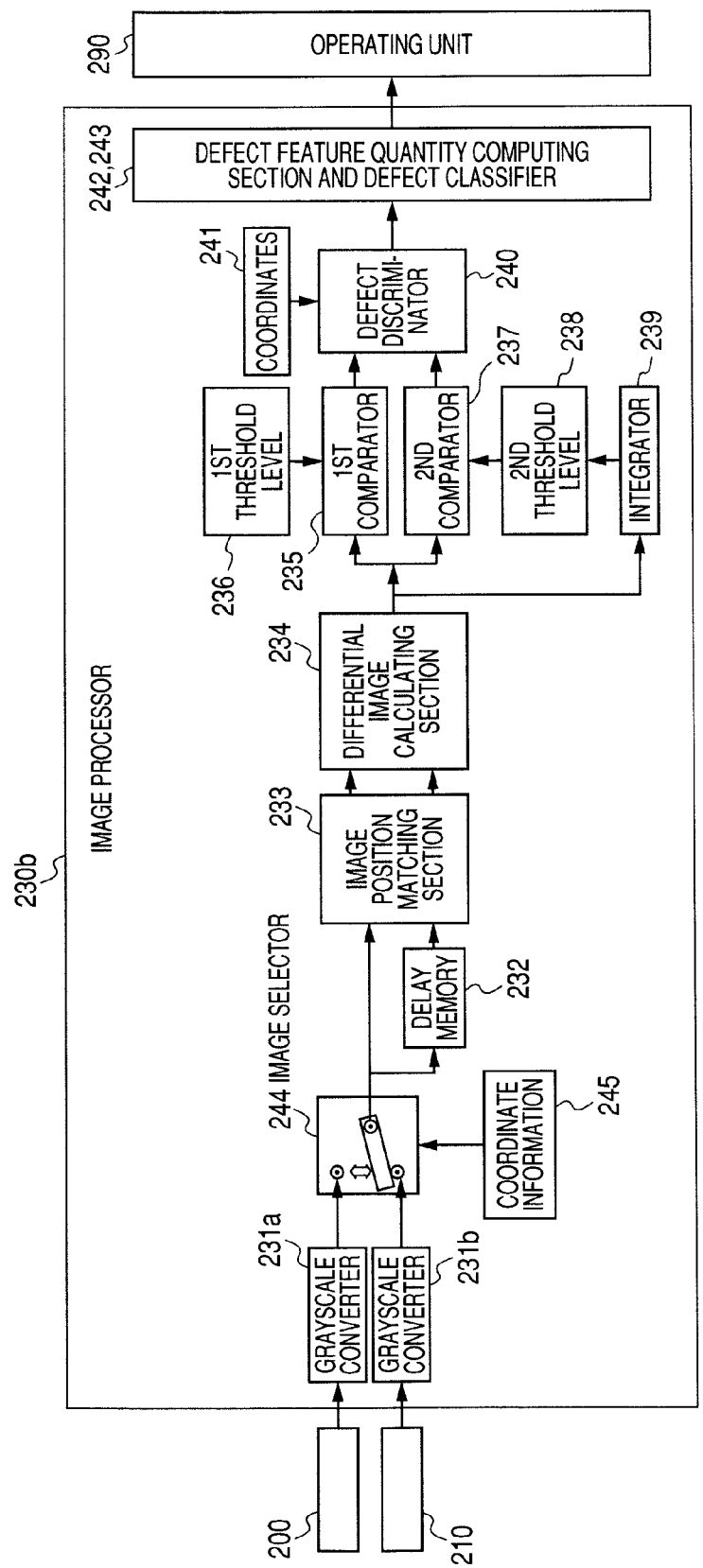
FIG. 9 is a block diagram showing a second example of an image processor used in the present invention.

Next, an example of smaller-scale image processing is described below using FIG. 9. More specifically, a process flow of acquiring an image of the memory block on the first detection optical path 21a described using FIG. 2, and detecting an image of the logic circuit block on the second detection optical path 21b, is described below. The first image sensor 200 and the second image sensor 210 detect images, regardless of the memory/logic region. For example, the resolution of the brightness of each detected image is expressed in 1,024 grayscale levels, and when the image is processed, the original grayscale level is converted into one of 256 grayscale levels. Linear or non-linear brightness conversion characteristics can be selected when the grayscale conversion is conducted. The grayscale converters 231*a* and 231*b* each conduct the grayscale conversion for each image signal and sends conversion results to an image selector 244. The image selector 244 receives the coordinate information 245 input from the stage 282, and can judge whether the input image relates to the memory block that is the periodic pattern block, or the logic circuit block that is the non-periodic pattern block. If the supplied image information relates to the memory block, the image selector selects the image signal detected by the first image sensor 200, or if the supplied image information relates to the logic circuit block, the image selector selects the image signal detected by the second image sensor 210. The image signal f1, f2 that has thus been selected is sent to both the image position-matching section 233 and the delay memory 232. The image that has been sent to the delay memory 232 is further sent to the image position-matching section 233, with a time-lag equivalent to, for example, the arrayal pitch of the dies on which the same pattern is formed. This time-lag is provided for reasons associated with design. Accordingly, the real-time detected image signal f1, f2 and a reference image signal g1, g2 relating to an adjacent die, for example, are sent to the image position-matching section 234, in which the two image signals are then matched in position and a differential image obtained by position matching of the two image signals is calculated by a differential image calculating section 234. The calculated differential image next undergoes two systems of threshold level processing in a first comparator 235 and a second comparator 237. The first comparator 235 uses a constant threshold level to conduct a first threshold level discrimination against, for example, absolute values of the memory block and logic circuit block differential images obtained from the differential image calculating section 234, and image feature quantities (brightness, size, and other information) in the region exceeding the threshold level are sent to a defect discriminator 240. Also, a second threshold level processor (integrator) 239 derives information, such as variations in brightness, from the differential images obtained from the differential image calculating section 234 after being detected, for example, in the memory region and the logic circuit region, and then generates a second threshold level 238 based on the derived image information such as the variations in brightness. The second comparator 237 compares the differential images obtained, for example, from the memory block and logic circuit block regions after processing in the differential image calculating sections 234, and the generated second threshold levels 238 relating to the memory block and logic circuit block regions. Each second threshold level 238 becomes a floating threshold level. As with the first threshold level, the image feature quantities in the region of the defect candidates exceeding the floating threshold level are sent to the defect discriminator 240. The image feature quantities that have been sent from the two systems are next used for the defect discriminator 240 to conduct synthetic defect discriminations, for example, in the memory block region and the logic circuit block region. At this time, since significant non-uniformity in brightness tends to exist for a specific pattern or other patterns, a normal section may be mis-discriminated as a defective. By utilizing the fact that the mis-discrimination easily occurs with a specific pattern 3, the inspection apparatus assigns coordinate information 241 of the wafer 1 to the defect discriminator 240, and sets up a flag to indicate that for the region in which the mis-discrimination is prone to occur, even if the above first or second threshold level is exceeded, the corresponding section will be excluded from the defect discrimination or the discrimination itself is most likely to result in an error. After the setup of the flag, the coordinate information is sent to the defect feature quantity computing section 242. The defect feature quantity computing section 242 uses detected images to calculate the feature quantities of defective sections even more closely than for the image feature quantities that have been sent to the comparators 235, 237. The defect classifier 243 uses the calculated feature quantities to classify the defects. The defect classification results, coordinate information, image feature quantities, and other information are output to the display device (or the like) of the operating unit 290.

Figure 10:
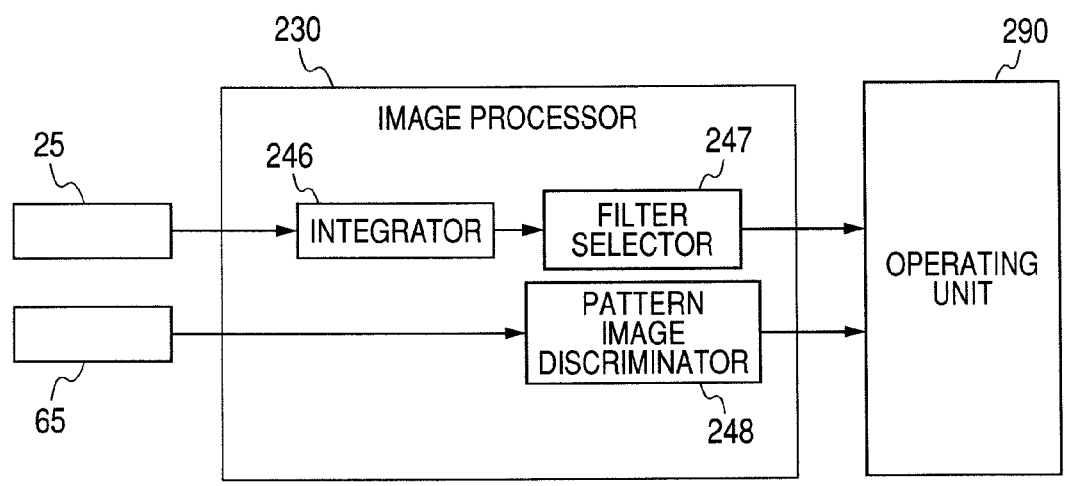
FIG. 10 is a diagram showing an example of an inspection recipe creation function of the image processor in the present invention.

Next, optical parameters relating to the darkfield detection optical system 20, that is, shield shapes of the spatial filters 50, 95, and setup parameters for the polarizers 30, 35, 80, 85 need to have respective appropriate parameter values selected according to the particular structure of the wafer 1, the particular shape of the pattern 3, the kind of defect 4 to be detected, and other factors. An inspection recipe also needs to be created using the operating unit 290. Functionality for creating this inspection recipe is described below using FIG. 10. As shown in FIG. 2, an image sensor 25*a*, 25*b* for observing a Fourier transform image required for the optical parameters for inspection, and a two-dimensional image sensor (two-dimensional camera) 65*a*, 65*b* for detecting a two-dimensional image of defects on the wafer 1 under a stationary state of the stage 282 are disposed in the darkfield detection optical system 20. Beam splitters 40*a*, 40*b* and 60*a*, 60*b* are disposed on each detection optical path (21*a*, 21*b*) so that light is distributed to both the Fourier transform plane observing image sensor 25*a*, 25*b* and the image sensor 65*a*, 65*b* during recipe creation. The two-dimensional image sensor (two-dimensional camera) 65*a*, 65*b* is disposed to reduce a time required for wafer scanning during acquisition of a two-dimensional image with the image sensor 200, 210. The two-dimensional image sensor 65*a*, 65*b* is also disposed to allow a recipe-creating person to easily select optical parameters by simultaneously observing an image of the Fourier transform plane and an image of the wafer 1 in real time. The beam splitter 60 and the two-dimensional image sensor (two-dimensional camera) 65 do not need to be provided on each detection optical path.

The image that the Fourier transform plane observing image sensor 25*a*, 25*b* has acquired is passed through an image adder (integrator) 246, and after another image has been added as necessary, both images are sent to a filter selector 247. The filter selector 247 selects a position of the Fourier transform plane to be optically shielded, then sends the coordinate data to the operating unit 290, and selects the spatial filter 50, 95 so that the selected region is optically shielded. Also, the image that the two-dimensional camera 65*a*, 65*b* has acquired is sent to a pattern image discriminator 248. Then the brightness, area, and other data of the pattern image are calculated from the detected darkfield image, and calculation results are sent to the operating unit 290.

Figure 11:
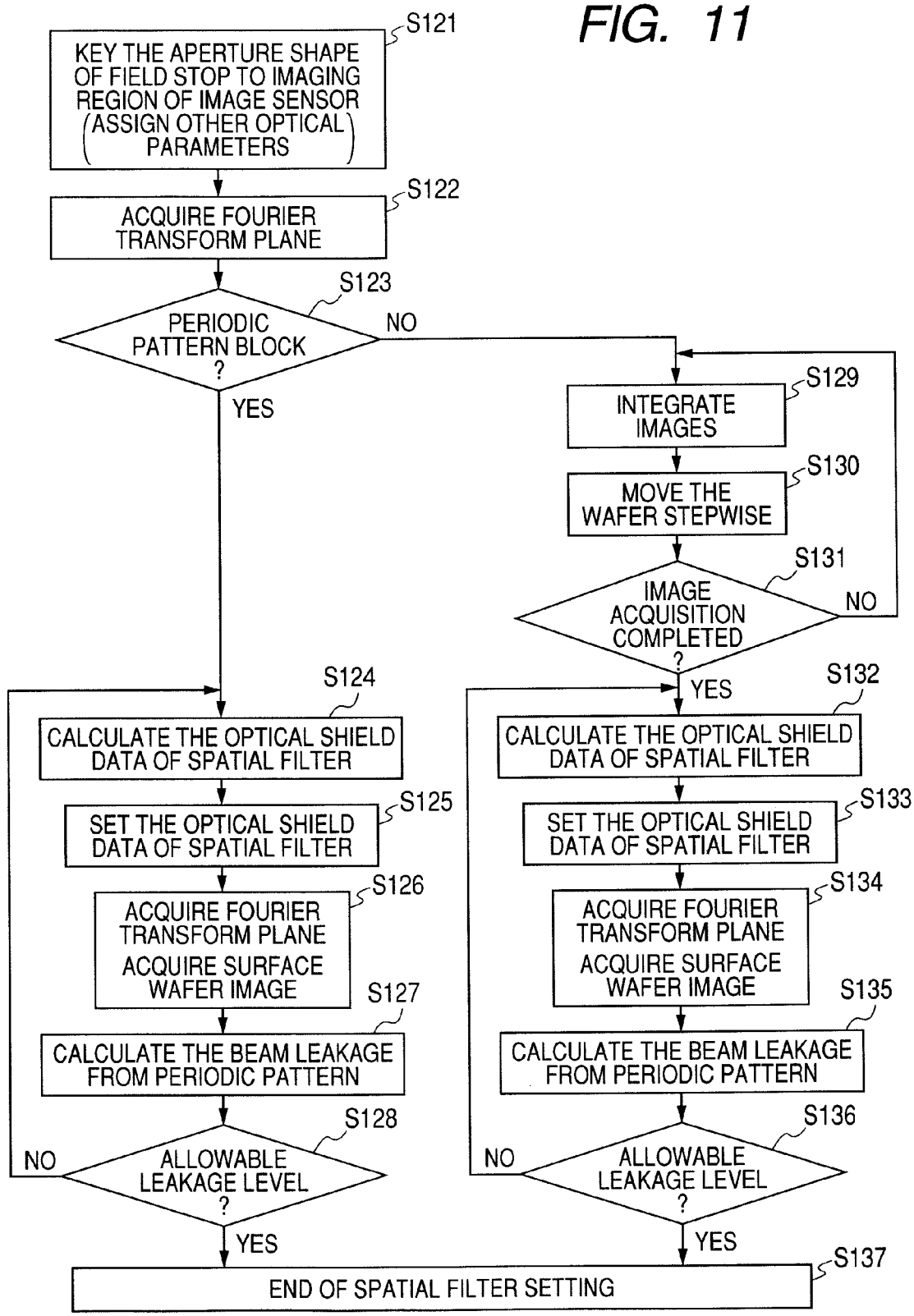
FIG. 11 is a flow diagram showing an example of a procedure for selecting a light-shielding element of a spatial filter in the present invention.

Next, a sequence for selecting an optical shield of the spatial filter 50, 95 by use of the above system is set forth below using FIG. 11. First in step S121, the wafer 1 is positioned for matching between an illumination area and a circuit pattern to be subjected to parameter setup, and an aperture shape of a field stop 26 with an on-wafer field size from 1 μm to 10 μm, shown in FIG. 2, is keyed to an imaging region of the image sensor 25*b*. Other optical parameters for illumination (namely, a selected wavelength band of the illumination light, the amount of illumination light, an elevation a of the linear beam 16, an illumination bearing, polarization of the illumination light, NA of the illumination light, and the like) are also assigned in step S121. Next in step S122, the image sensor (TV camera) 25a, 25b acquires a Fourier transform image. Next in step S123, periodicity discriminator (pattern image discriminator) 247 discriminates whether the spatial filtering parameter setup area is a periodic pattern block. If the area is a periodic pattern block and the Fourier transform image lacks brightness, the amount of illumination light (e.g., a laser output level) to be applied from the darkfield illumination optical system 10 is increased or the brightness of the image is adjusted to an appropriate level by adding a plurality of images in the image adder (integrator) 245. In step S124, the image that has thus been enhanced in brightness is sent to the filter selector 246, a region of a diffraction image is calculated, and parameters relating to operating equally pitched linear spatial filters for optically shielding the region of the diffraction image are determined by calculation. In step S125, the thus-obtained information is sent to the operating unit 290 and the first spatial filter 50 is set via the mechanism controller 280. In order to judge adequacy of these setting results, the TV camera 25a confirms in step S126 that the diffraction image of the periodic circuit pattern is optically shielded. Additionally in step S126, TV camera 65a acquires the wafer image and confirms that the brightness of the periodic circuit pattern is suppressed. Beam leakage from the diffraction image of the periodic circuit pattern is calculated in step S127, and if, in step S128, the calculated beam leakage level is judged not to be within an allowable range (i.e., the diffraction image is not fully shielded), process control is returned to step S124, in which step, parameters relating to the equally pitched linear spatial filters are then determined and the old parameter data therefor is changed. That is to say, this operation sequence is repeated until the optically shielded state of the diffraction image of the periodic circuit pattern has fallen within the allowable range in step S128.

Next, a setting sequence relating to the apertured non-periodic spatial filter and other optical elements set if, in step S123, the spatial filter parameter setup area is judged to be a non-periodic circuit pattern by the periodicity discriminator (pattern image discriminator) 247, is set forth below. Basically, the apertured non-periodic spatial filter and other optical elements are set using the same sequence as that of the periodic circuit pattern. The non-periodic circuit pattern is dissimilar to the periodic circuit pattern in that orientation of the former differs according to position on the wafer. It is desirable, therefore, that a total diffraction image of the non-periodic pattern block be acquired and that the shape of the aperture 96 of the second spatial filter 95 be determined from that image. In order to conduct these, in step S130, the wafer is moved stepwise to a position at which the orientation of the circuit pattern differs, then in step S131, Fourier transform images are acquired using the beam splitter 40b, imaging lens 27b, and TV camera 25b provided on the second detection optical path 21b, and in step S129, the acquired images are added in the image adder (integrator) 246. This sequence is repeated until image acquisition in a previously designated image acquisition region has ended. Brightness of the image obtained by the addition is given primarily by the light scattered from the circuit pattern. A region brighter than the obtained image is selected (optical shield data of a spatial filter is calculated) in step S132. In step S133, an apertured non-periodic spatial filter of an appropriate shield shape is selected from the apertured non-periodic spatial filters provided beforehand for optically shielding the above-selected region, and the selected spatial filter is set. In order to judge adequacy of these filter selection results, the TV camera 25b confirms in step S134 that the non-periodic scattered-beam image 3r, 3s shown in FIG. 5A is optically shielded. Additionally in step S134, the TV camera 65a acquires the wafer image and confirms that the brightness of the non-periodic scattered-beam image is suppressed. Beam leakage from the non-periodic scattered-beam image is calculated in step S135, and if, in step S136, the calculated beam leakage level is judged not to be within an allowable range (i.e., the diffraction image is not shielded), process control is returned to step S132, in which step, parameters relating to the apertured non-periodic spatial filters 95 are then determined and the old parameter data therefor is changed. That is to say, this operation sequence is repeated until the optically shielded state of the scattered-beam image of the non-periodic circuit pattern has fallen within the allowable range in step S136. Thus, setting of the spatial filters 50, 95 is completed in step S137.

Figure 12:
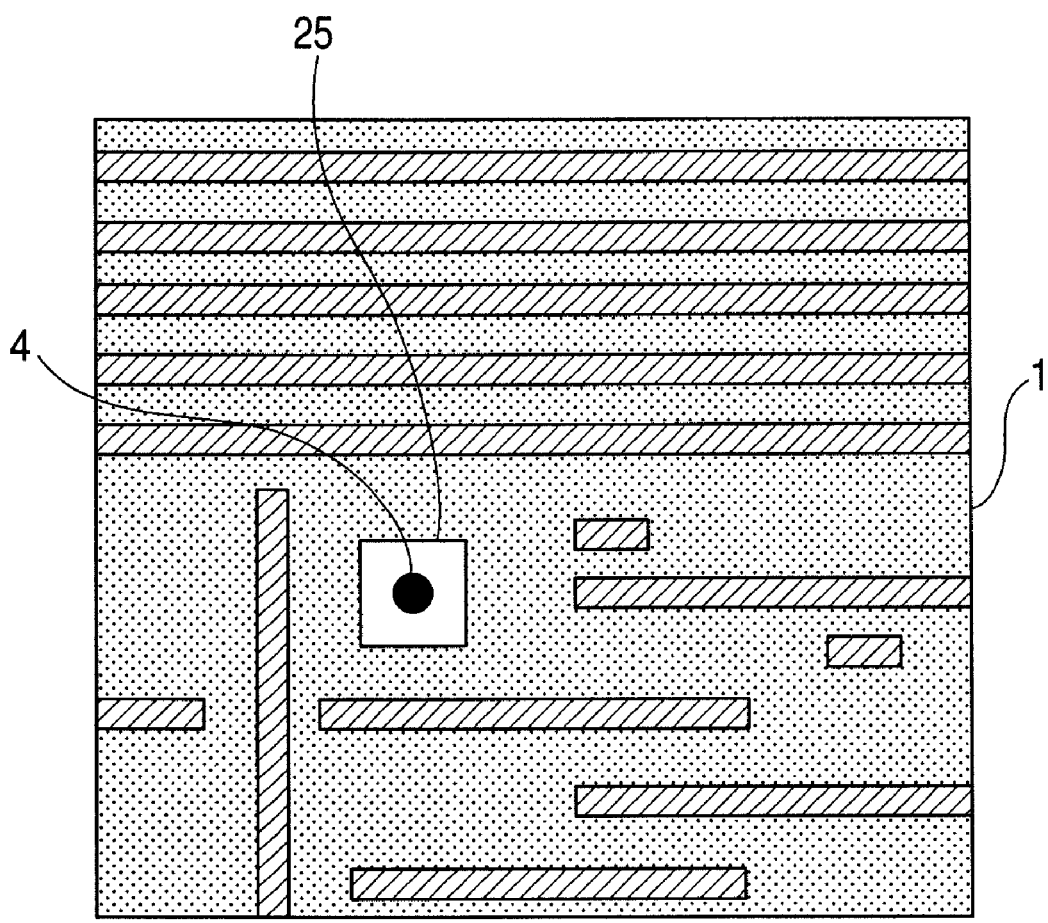
FIG. 12 is an explanatory diagram of field stop setting according to the present invention.
Figure 13:
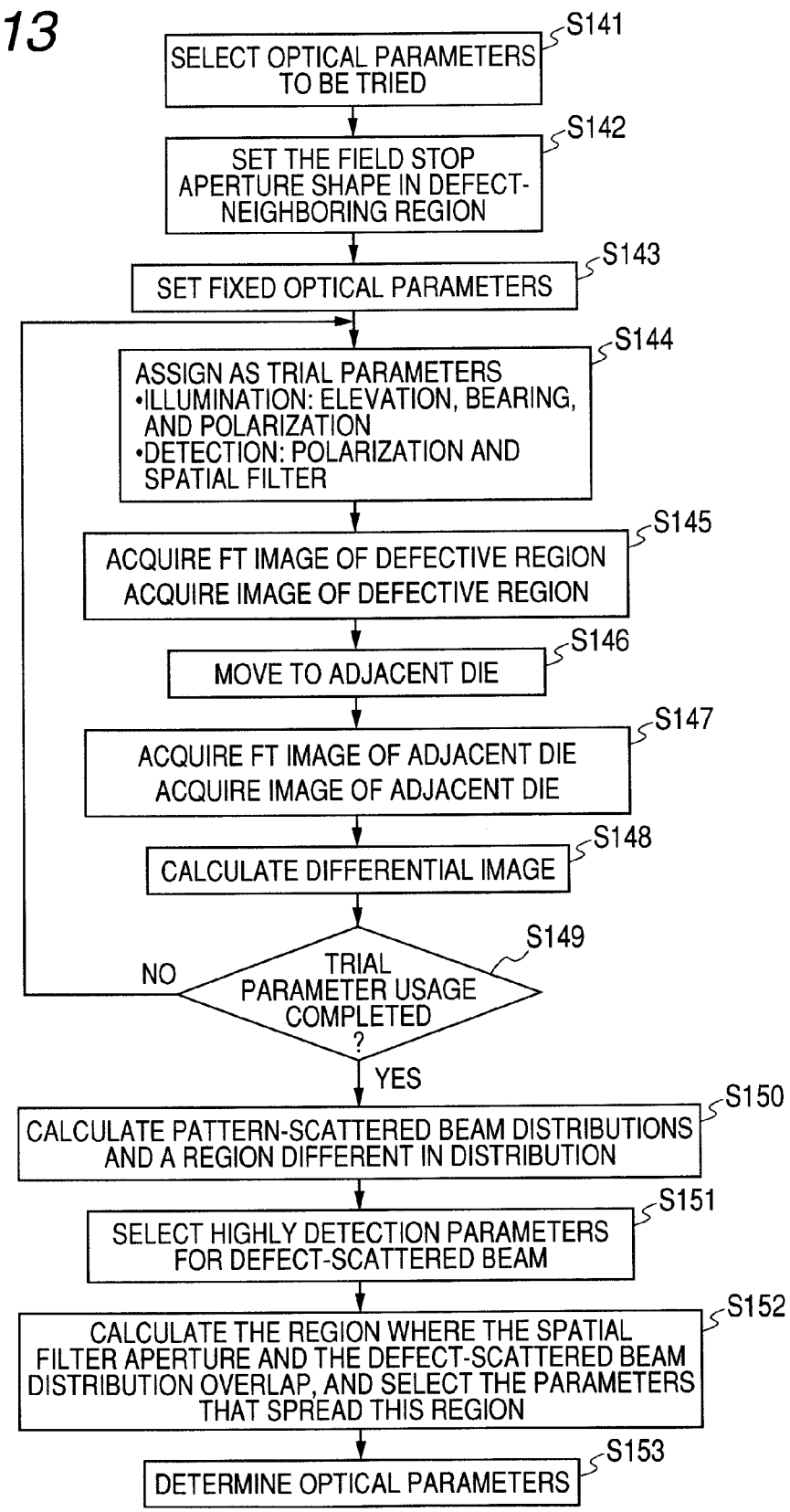
FIG. 13 is a flow diagram showing an example of a procedure for assigning optical parameters in the present invention.

Next, a method for optimizing various optical parameters to detect a specific defect highly critical to a device is described below using FIGS. 12 and 13. FIG. 12 shows a plan view of the wafer 1. Defect 4 is a defect to be detected in a non-periodic pattern region. To optimize a spatial filter, it is necessary to understand a scattered-beam distribution of the defect. Illumination light is emitted in a wide range, so to detect the scattered-beam distribution of the defect 4 only, an aperture shape needs to be set only in neighborhood of the defective region by use of the field stop 26 disposed in the darkfield detection optical system 20 of FIG. 2. A size of this aperture changes according to that of the defect and a positional relationship with respect to a peripheral pattern. The field stop 26 has an appropriate on-wafer aperture size of about 1 to 10 μm per side for an LSI pattern (this on-wafer aperture size corresponds to an outside diameter of a circular aperture). A distribution of the scattered light detected by the Fourier transform image observing camera 25b via the field stop 26 of the darkfield detection optical system 20 is a distribution of the light scattered mainly from the defect, so setting the apertured non-periodic spatial filter 95 at a position high in luminance of the scattered light makes it possible to detect the light scattered from the defect, and suppress the light scattered from normal non-periodic patterns.

Next, a sequence relating to optimizing optical parameters for a defect that is to be detected is described below using FIG. 13. In step S141, optical parameters to be first used for trial are selected using the GUI of the operating unit 290. Next in step S142, the aperture shape of the field stop 26 in the darkfield detection optical system 20 is set in the neighborhood of the defect on the basis of the screen shown in FIG. 12. Next in step S143, fixed optical parameters (a wavelength band of the illumination light, the amount of illumination light, an imaging magnification of the imaging lens set 55, 57 or 100, 110, and other parameters) are set using the GUI of the operating unit 290. Next, optical parameters to be tried are set in step S144.

Roughly two sets of parameters are usable for trial. One set relates to the darkfield illumination optical system 10, and this set includes, for example, the elevation a of the illumination light (slit-shaped beam) 16 (i.e., the angle of the optical axis of the illumination light 16 from the wafer surface), an angle with respect to a reference illumination bearing (e.g., a notch direction of the wafer) or an angle with respect to a traveling direction (when used as a reference direction) of the X-stage 282 of the apparatus, polarization of the illumination light, and the NA of the illumination light. The other parameter set relates to the darkfield detection optical system 20 and includes, for example, rotational angles of the quarter-wavelength plate 30, 80 and polarizer 35, 85, and the aperture shape and double-refractor of the spatial filter 95 (the parameters relating to this spatial filter are selected after the determination of the above parameters).

These parameters are assigned and optimization is executed using the following loop.

In step S145, the camera 25b, 65b acquires a darkfield image and Fourier transform image of a defective region, and in step S146, the wafer is moved to an adjacent die. On this die, the camera 25b, 65b also acquires a darkfield image and Fourier transform image of a normal region in step S147. Next in step S148, the image processor 230 calculates a differential image from the darkfield image and Fourier transform image of the adjacent die. In step S149, it is judged whether trial parameter data execution with the operating unit 290 has been completed. If the execution is not completed, process control is returned to step S144 and then steps up to S148 are repeated. Next in step S150, the image processor 230 compares the scattered-beam distribution of the defective region and that of the normal region based on the differential image of the Fourier transform images associated with the executed trial parameters, and calculates a region different in the distribution. At this time, the region different between the defective and normal regions in terms of the scattered-beam distribution is discriminated by utilizing, for example, the differential image of the Fourier transform images. The region different in the scattered-beam distribution is, for example, the region where the light scattered from the defective section is relatively strong when compared with the light scattered from the normal section, or the region where the light scattered from the defective section is present in a region free from the light scattered from the normal section. Thus, an optical parameter that allows efficient detection of a larger amount of light scattered from the defect is confirmed and selected in step S151. The number of parameters selected in this step may be two or more, not one. The image processor 230 can thus confirm the optical parameter that allows the detection of a larger amount of light scattered, and a position on the Fourier transform plane where the light scattered occurs. Next in step S152, the image processor 230 selects the apertured non-periodic type of spatial filter 95 apertured at the position on the Fourier transform plane where the light scattered occurs, and supplies the information to the operating unit 290. This completes the selection of the appropriate optical parameter for the apertured non-periodic type of spatial filter, pursuant to the control of the mechanism controller 280 that is based on a control command from the operating unit 290. If the number of selected parameters is plural, test inspection with the selected parameters is conducted and then an appropriate parameter that allows higher performance to be obtained during the detection of defects and the discrimination of normal patterns is selected according to test inspection results. Thus, optical parameter setup is completed in step S153.

While various combinations are possible for the above-described configuration, functionality, and parameterization, it is obvious that the combinations also stay within the scope of the present invention.

Of all the aspects of the present invention that have been disclosed in the above examples, some of typical aspects are summarized below.

(1) A defect inspection apparatus includes:
a darkfield illumination optical system that conducts darkfield illumination upon the surface of a sample with irradiation light having a plurality of wavelength bands;
a darkfield detection optical system that includes a reflecting objective lens for converging the light scattered from the surface of the sample that has been darkfield-illuminated with the irradiation light having the plurality of wavelength bands, and wavelength separation optics for conducting wavelength separation of the scattered light that has been converged by the reflecting objective lens, and after the wavelength separation, branching the scattered light into at least a first detection optical path and a second detection optical path, the darkfield detection optical system further having, on the first detection optical path, a first spatial filter for optically shielding, of all the first scattered light having the wavelength band which has been selected by the wavelength separation optics, only a diffraction image arising from a periodic circuit pattern formed on the surface of the sample, and first imaging optics for imaging onto a light-receiving surface of a first image sensor the first scattered light that has been passed through the first spatial filter, and the darkfield detection optical system further having, on the second detection optical path, a second spatial filter for optically shielding, of all the second scattered light having the wavelength band which has been selected by the wavelength separation optics, only a region high in an intensity distribution of the scattered light arising from a non-periodic circuit pattern formed on the surface of the sample, and second imaging optics for imaging onto a light-receiving surface of a second image sensor the second scattered light that has been passed through the second spatial filter; and an image processor which, in accordance with a first image signal obtained from the first image sensor of the darkfield detection optical system, or/and a second image signal obtained from the second image sensor, discriminates defects or defect candidates present on the surface of the sample.

(2) Another defect inspection apparatus includes:
a darkfield illumination optical system that conducts darkfield illumination upon the surface of a sample with irradiation light having a plurality of wavelength bands;
a darkfield detection optical system that includes a reflecting objective lens for converging the light scattered from the surface of the sample that has been darkfield-illuminated with the irradiation light having the plurality of wavelength bands, and branching optics for branching the scattered light that the reflecting objective lens has converged, into at least a first detection optical path and a second detection optical path, the foregoing darkfield detection optical system further having, on the first detection optical path, a first wavelength selection filter for selecting a first wavelength band from a distribution of the scattered light which has been branched by the branching optics, and first imaging optics for imaging onto a light-receiving surface of a first image sensor the first scattered light having the first wavelength band which has been selected by the first wavelength selection filter, and the darkfield detection optical system further having, on the second detection optical path, a second wavelength selection filter for selecting a second wavelength band from the distribution of the scattered light which has been branched by the branching optics, and second imaging optics for imaging onto a light-receiving surface of a second image sensor the second scattered light having the second wavelength band which has been selected by the second wavelength selection filter; and an image processor which, in accordance with a first image signal obtained from the first image sensor of the darkfield detection optical system, or/and a second image signal obtained from the second image sensor, discriminates defects or defect candidates present on the surface of the sample.

(3) Yet another defect inspection apparatus includes:
a darkfield illumination optical system that conducts darkfield illumination upon the surface of a sample with irradiation light having a plurality of wavelength bands;
a darkfield detection optical system that includes a reflecting objective lens for converging the light scattered from the surface of the sample that has been darkfield-illuminated with the irradiation light having the plurality of wavelength bands, and branching optics for branching the scattered light that the reflecting objective lens has converged, into at least a first detection optical path and a second detection optical path, the foregoing darkfield detection optical system further having, on the first detection optical path, a first wavelength selection filter for selecting a first wavelength band from a distribution of the scattered light which has been branched by the branching optics, a first spatial filter for optically shielding, of all the first scattered light having the first wavelength band which has been selected by the first wavelength selection filter, only a diffraction image arising from a periodic circuit pattern formed on the surface of the sample, and first imaging optics for imaging onto a light-receiving surface of a first image sensor the first scattered light which has been passed through the first spatial filter, and the darkfield detection optical system further having, on the second detection optical path, a second wavelength selection filter for selecting a second wavelength band from the distribution of the scattered light which has been branched by the branching optics, a second spatial filter for optically shielding, of all the second scattered light having the second wavelength band which has been selected by the second wavelength selection filter, only a region high in an intensity distribution of the scattered light arising from a non-periodic circuit pattern formed on the surface of the sample, and second imaging optics for imaging onto a light-receiving surface of a second image sensor the second scattered light which has been passed through the second spatial filter; and an image processor which, in accordance with a first image signal obtained from the first image sensor of the darkfield detection optical system, or/and a second image signal obtained from the second image sensor, discriminates defects or defect candidates present on the surface of the sample.

(4) The darkfield detection optical system of the defect inspection apparatus described in above item (2) further has a first polarizing filter on the first detection optical path and a second polarizing filter on the second detection optical path.

(5) The darkfield detection optical system of the defect inspection apparatus described in above item (2) further has an ND filter to reduce the light in intensity, on the first detection optical path or the second detection optical path.

(6) The image processor of the defect inspection apparatus described in above item (2) selects the first image signal or the second image signal, depending upon at least whether the circuit pattern of interest, formed on the surface of the sample, has periodicity, and then discriminates the defects or the defect candidates.

(7) A further defect inspection apparatus includes:
a darkfield illumination optical system that conducts darkfield illumination upon the surface of a sample with irradiation light having a plurality of wavelength bands;
a darkfield detection optical system that includes a reflecting objective lens for converging the light scattered from the surface of the sample that has been darkfield-illuminated with the irradiation light having the plurality of wavelength bands, and branching optics for branching the scattered light that the reflecting objective lens has converged, into at least a first detection optical path and a second detection optical path, the foregoing darkfield detection optical system further having, on the first detection optical path, a first spatial filter for optically shielding the light diffracted from a periodic circuit pattern formed on the surface of the sample, and first imaging optics for imaging onto a light-receiving surface of a first image sensor the first scattered light which has been passed through the first spatial filter, and the darkfield detection optical system further having, on the second detection optical path, a second spatial filter for optically shielding a region high in an intensity distribution of the scattered light arising from a non-periodic circuit pattern formed on the surface of the sample, second imaging optics for imaging onto a light-receiving surface of a second image sensor the second scattered light which has been passed through the second spatial filter, and an ND filter for reducing the light in intensity on the first detection optical path or on the second detection optical path; and an image processor which, in accordance with a first image signal obtained from the first image sensor of the darkfield detection optical system, or/and a second image signal obtained from the second image sensor, discriminates defects or defect candidates present on the surface of the sample.

(8) The darkfield detection optical system of the defect inspection apparatus described in above item (7) further has a first polarizer on the first detection optical path and a second polarizer on the second detection optical path.

(9) The light-receiving surfaces of the first and second image sensors in the darkfield detection optical system of the defect inspection apparatus described in above item (7) are each formed into a rectangular shape, and the irradiation light in the darkfield illumination optical system is a slit-shaped beam keyed to the rectangular field shape of the light-receiving surfaces.

(10) The image processor of the defect inspection apparatus described in above item (7) selects the first image signal or the second image signal, depending upon at least whether the circuit pattern of interest, formed on the surface of the sample, has periodicity, and then discriminates the defects or the defect candidates.

(11) The reflecting objective lens in the defect inspection apparatus described in above item (7) has an NA of 0.6 or more.

(12) A further defect inspection apparatus includes:
a darkfield illumination optical system which, after rectangularly shaping an illumination beam of light, conducts darkfield illumination upon the surface of a sample from an oblique direction;
a darkfield detection optical system adapted to
include an objective lens for converging the light scattered from the surface of the sample that has been darkfield-illuminated by the darkfield illumination optical system, and branching optics for branching the converged light into a first detection optical path and a second detection optical path,
have, on the first detection optical path formed by the branching optics, a first spatial filter and a first polarizer, either or both of which are controlled in terms of setting state such that characteristics of the scattered light passed through will differ from each other, a first imaging lens for imaging the scattered light which has been passed through the first spatial filter and the first polarizer, and a first image sensor for receiving the scattered-light image which has been formed via the first imaging lens,
have, on the second detection optical path formed by the branching optics, a second spatial filter and a second polarizer, either or both of which are controlled in terms of setting state such that the characteristics of the scattered light passed through will differ from each other, a second imaging lens for imaging the scattered light which has been passed through the second spatial filter and the second polarizer, and a second image sensor for receiving the scattered-light image which has been formed via the second imaging lens, and have, on at least either of the first and second detection optical paths, an ND filter for reducing the light in intensity;

a focusing unit for setting a focal position of the darkfield detection optical system to the surface of the sample; and an image processor which, in accordance with an image signal obtained from the first image sensor on the first detection optical path of the darkfield detection optical system or from the second image sensor on the second detection optical path of the darkfield detection optical system, discriminates defects or defect candidates present on the surface of the sample.

As described above, according to the present invention, defects present on a mixed-type wafer (such as system LSI) or the like, inclusive of a memory block with a periodic circuit pattern formed thereon, and of a logic circuit block with an irregular (non-periodic) circuit pattern formed thereon, can be detected with high sensitivity. Also, a wide variety of defect species can be detected and a defect detection ratio improved.

In addition, the reflecting objective lens in the present invention has an NA (Numerical Aperture) equal to or greater than 0.6, but less than 1.0.

Furthermore, during darkfield detection based on darkfield illumination, the amount of light detected on a periodic circuit pattern and a non-periodic circuit pattern can be maintained at an appropriate level, irrespective of whether the circuit pattern of interest, formed on the wafer, has periodicity. Moreover, inspection sensitivity can be enhanced for both the periodic circuit pattern and the non-periodic circuit pattern.

The invention may be embodied in other specific forms without departing from the spirit or essential characteristics thereof. The present embodiment is therefore to be considered in all respects as illustrative and not restrictive, the scope of the invention being indicated by the appended claims, rather than by the foregoing description, and all changes that come within the meaning and range of equivalency of the claims are therefore intended to be embraced therein.

The invention claimed is:

1. A defect inspection apparatus comprising:
an illumination optical system which conducts illumination upon the surface of a sample with irradiation light;
a detection optical system which includes a reflecting objective lens for converging light scattered from the surface of the sample that has been illuminated by the illumination optical system, and wavelength separation optics for conducting wavelength separation of the scattered light that has been converged by the reflecting objective lens, and after the wavelength separation, branching the scattered light into at least a first detection optical path and a second detection optical path, wherein the detection optical system further includes, on the first detection optical path, a first optics for collecting onto a light-receiving surface of a first sensor the first scattered light having a wavelength band which has been selected by the wavelength separation optics, and wherein the detection optical system further includes, on the second detection optical path, second optics for collecting onto a light-receiving surface of a second sensor the second scattered light having a wavelength band which has been selected by the wavelength separation optics; and
a signal processor which, in accordance with at least one of a first signal obtained from the first sensor of the detection optical system and a second signal obtained from the second sensor, discriminates defects or defect candidates present on the surface of the sample.

2. The defect inspection apparatus according to claim 1, wherein:
the detection optical system further includes a first polarizing filter disposed on the first detection optical path, and a second polarizing filter disposed on the second detection optical path.

3. The defect inspection apparatus according to claim 1, wherein:
the detection optical system further includes an ND filter disposed on at least one of the first detection optical path and the second detection optical path in order to reduce the light in intensity.

4. The defect inspection apparatus according to claim 1, wherein:
the signal processor selects at least one of the first signal and the second signal, depending upon at least whether the circuit pattern of interest, formed on the surface of the sample, has periodicity, and then discriminates the defects or the defect candidates.

5. The defect inspection apparatus according to claim 1, wherein:
the light-receiving surfaces of the first sensor and second sensor in the detection optical system are each formed into a rectangular shape, and;
the irradiation light in the illumination optical system is a slit-shaped beam keyed to the rectangular field shape of the light-receiving surfaces.

6. The defect inspection apparatus according to claim 1, wherein:
the detection optical system further includes a focusing mechanism to set a focal position of the detection optical system to the surface of the sample.

7. A defect inspection apparatus comprising:
an illumination optical system which, after rectangularly shaping irradiation light, irradiates the surface of a sample from an oblique direction;
a detection optical system which includes a reflecting objective lens for converging light scattered from the surface of the sample that has been illuminated by the illumination optical system, and branching optics for branching scattered light that has been converged by the reflecting objective lens, into at least a first detection optical path and a second detection optical path, wherein the detection optical system is adapted to cause at least one of a spatial filter and a polarizer to differ in setting state between the first detection optical path and the second detection optical path so that the scattered beams of light, obtained on the detection optical paths, will differ from each other in characteristics;
wherein the detection optical system further includes, on the first detection optical path, a first spatial filter and a first polarizer, on the second detection optical path, a second spatial filter and a second polarizer, and on at least either of the first and second detection optical paths, an ND filter; and
wherein the detection optical system further includes, on the first detection optical path, first optics for collecting onto a light-receiving surface of a first sensor the first scattered light obtained after being passed through the first spatial filter and the first polarizer, and on the second detection optical path, second optics for collecting onto a light-receiving surface of a second sensor the second scattered light obtained after being passed through the second spatial filter and the second polarizer; and
a signal processor which, in accordance with at least one of a first signal obtained from the first sensor of the detection optical system and a second signal obtained from the second sensor, discriminates defects or defect candidates present on the surface of the sample.

8. The defect inspection apparatus according to claim 7, wherein:
the light-receiving surfaces of the first sensor and second sensor in the detection optical system are each formed into a rectangular shape, and;
the detection optical system further includes at least one of a non-spherical lens and a non-spherical mirror that shapes the irradiation light into a slit-shaped beam keyed to the rectangular field shape of the light-receiving surfaces.

9. The defect inspection apparatus according to claim 7, wherein:
in the detection optical system, a field stop that permits the scattered light in a field size range from 1 μm to 10 μm on the sample to pass through is disposed at least one of on the first detection optical path and on the second detection optical path, the at least one of the first spatial filter and the second spatial filter is disposed at a position of an image surface side of the field stop from the field stop, a Fourier transform plane is formed at a position of an image surface side of the at least one of the first spatial filter and the second spatial filter, and an image sensor is disposed at the position of the formed Fourier transform plane.

10. The defect inspection apparatus according to claim 7, wherein the first polarizer and the second polarizer each includes a quarter-wavelength plate.

11. The defect inspection apparatus according to claim 7, wherein the second spatial filter is formed into a type including a plurality of non-periodic apertures and has a double-refracting material in a part of the plural apertures.

* * * * *